(12) United States Patent
Chumsae

(10) Patent No.: US 9,193,787 B2
(45) Date of Patent: Nov. 24, 2015

(54) HUMAN ANTIBODIES THAT BIND HUMAN TNF-ALPHA AND METHODS OF PREPARING THE SAME

(71) Applicant: ABBVIE INC., North Chicago, IL (US)

(72) Inventor: Christopher M. Chumsae, North Andover, MA (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 14/522,535

(22) Filed: Oct. 23, 2014

(65) Prior Publication Data

US 2015/0045542 A1 Feb. 12, 2015

Related U.S. Application Data

(60) Division of application No. 14/078,181, filed on Nov. 12, 2013, and a continuation-in-part of application No. 13/803,808, filed on Mar. 14, 2013, and a continuation-in-part of application No. 13/830,976, filed on Mar. 14, 2013, said application No. 14/078,181 is a continuation-in-part of application No. 13/829,989, filed on Mar. 14, 2013, which is a continuation-in-part of application No. 13/830,583, filed on Mar. 14, 2013.

(60) Provisional application No. 61/777,883, filed on Mar. 12, 2013, provisional application No. 61/696,207, filed on Sep. 2, 2012, provisional application No. 61/636,469, filed on Apr. 20, 2012, provisional application No. 61/636,511, filed on Apr. 20, 2012, provisional application No. 61/636,493, filed on Apr. 20, 2012.

(51) Int. Cl.
C07K 1/18 (2006.01)
C07K 16/24 (2006.01)

(52) U.S. Cl.
CPC ............... *C07K 16/241* (2013.01); *C07K 1/18* (2013.01); *C07K 2317/40* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| RE30,985 E | 6/1982 | Cartaya | |
| 4,399,216 A | 8/1983 | Axel et al. | |
| 4,510,245 A | 4/1985 | Cousens et al. | |
| 4,560,655 A | 12/1985 | Baker | |
| 4,634,665 A | 1/1987 | Axel et al. | |
| 4,657,866 A | 4/1987 | Kumar | |
| 4,767,704 A | 8/1988 | Cleveland et al. | |
| 4,801,687 A | 1/1989 | Ngo | |
| 4,816,397 A | 3/1989 | Boss et al. | |
| 4,877,608 A | 10/1989 | Lee et al. | |
| 4,927,762 A | 5/1990 | Darfler | |
| 4,933,435 A | 6/1990 | Ngo | |
| 4,968,615 A | 11/1990 | Koszinowski et al. | |
| 5,045,468 A | 9/1991 | Darfler | |
| 5,096,816 A | 3/1992 | Maiorella | |
| 5,110,913 A | 5/1992 | Coan et al. | |
| 5,118,796 A | 6/1992 | Prior et al. | |
| 5,122,469 A | 6/1992 | Mather et al. | |
| 5,126,250 A | 6/1992 | McDonough et al. | |
| 5,168,062 A | 12/1992 | Stinski | |
| 5,179,017 A | 1/1993 | Axel et al. | |
| 5,231,024 A | 7/1993 | Moeller et al. | |
| 5,328,985 A | 7/1994 | Sano et al. | |
| 5,378,612 A | 1/1995 | Nakashima et al. | |
| 5,429,746 A | 7/1995 | Shadle et al. | |
| 5,530,101 A | 6/1996 | Queen et al. | |
| 5,545,403 A | 8/1996 | Page | |
| 5,545,806 A | 8/1996 | Lonberg et al. | |
| 5,545,807 A | 8/1996 | Surani et al. | |
| 5,561,053 A | 10/1996 | Crowley | |
| 5,569,825 A | 10/1996 | Lonberg et al. | |
| 5,625,126 A | 4/1997 | Lonberg et al. | |
| 5,633,162 A | 5/1997 | Keen et al. | |
| 5,633,425 A | 5/1997 | Lonberg et al. | |
| 5,644,036 A | 7/1997 | Ramage et al. | |
| 5,654,407 A | 8/1997 | Boyle et al. | |
| 5,656,272 A | 8/1997 | Le et al. | |
| 5,661,016 A | 8/1997 | Lonberg et al. | |
| 5,672,347 A | 9/1997 | Aggarwal et al. | |
| 5,672,502 A | 9/1997 | Birch et al. | |
| 5,698,195 A | 12/1997 | Le et al. | |

(Continued)

FOREIGN PATENT DOCUMENTS

CN 1563090 A 1/2005
DE 3631229 A1 3/1988

(Continued)

OTHER PUBLICATIONS

Khawli et al. Charge variants in IgG1: Isolation, characterization, in vitro binding properties and pharmacokinetics in rats. MAbs. Nov.-Dec. 2010;2(6):613-24. Epub Nov. 1, 2010.*
Mehta et al. Purifying Therapeutic Monoclonal Antibodies. Chemical Engineering Progress. May 2008;104(5):S14-S20.*
Roe, S. "Separation Based on Structure" Chapter 4, § 5.2, In, Protein Purification Methods: A Practical Approach, Harris et al. (Eds.), Sep. 1989, IRL Press, Oxford, UK, p. 203.*
"Memorandum in Support of Centocor's Motion for Summary Judgment No. 1 that All Asserted Claims are Invalid for Lack of Written Description", dated Aug. 1, 2013 and submitted by defendant in Civil Action No. 09-40089-FDS, 28 pages.

(Continued)

*Primary Examiner* — David Romeo
(74) *Attorney, Agent, or Firm* — Sterne, Kessler, Goldstein & Fox P.L.L.C.

(57) ABSTRACT

Methylglyoxal (MGO)-modified recombinant TNF-alpha antibodies (e.g., Adalimumab) are identified. MGO modification decreases binding between Adalimumab and TNF-alpha. Methods are disclosed for reducing the presence of MGO-modified antibodies in the production of Adalimumab TNF-alpha antibodies.

29 Claims, 12 Drawing Sheets

(56) References Cited

U.S. PATENT DOCUMENTS

| | | |
|---|---|---|
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 9,017,687 B1 | 4/2015 | Wang et al. |
| 9,062,106 B2 | 6/2015 | Bengea et al. |
| 9,067,990 B2 | 6/2015 | Wang et al. |
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |

(56) References Cited

U.S. PATENT DOCUMENTS

| | | |
|---|---|---|
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0172911 A1 | 7/2010 | Naso et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0093810 A1 | 4/2012 | Takeda et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0244280 A1 | 9/2013 | Parikh et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |

(56) References Cited

U.S. PATENT DOCUMENTS

| | | |
|---|---|---|
| 2014/0141007 A1 | 5/2014 | Fraunhofer et al. |
| 2014/0141008 A1 | 5/2014 | Fraunhofer et al. |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1 | 9/2014 | Nti-gyabaah et al. |
| 2014/0301977 A1 | 10/2014 | Nadarajah et al. |
| 2014/0314745 A1 | 10/2014 | Rives et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0132320 A1 | 5/2015 | Chumsae et al. |
| 2015/0132801 A1 | 5/2015 | Ramasubramanyan et al. |
| 2015/0140006 A1 | 5/2015 | Ramasubramanyan et al. |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |

FOREIGN PATENT DOCUMENTS

| | | |
|---|---|---|
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 | 4/2011 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 A1 | 1/2015 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |
| WO | WO-99/32605 A1 | 7/1999 |
| WO | WO-99/57134 A1 | 11/1999 |
| WO | WO-99/57246 A1 | 11/1999 |
| WO | WO-0003000 A2 | 1/2000 |
| WO | WO-01/44442 A1 | 6/2001 |
| WO | WO-01/47554 A1 | 7/2001 |
| WO | WO-01/59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03/045995 A2 | 6/2003 |
| WO | WO-03/059935 A2 | 7/2003 |
| WO | WO-03/066662 A2 | 8/2003 |
| WO | WO-2004/008100 A2 | 1/2004 |
| WO | WO-2004/058800 A2 | 7/2004 |
| WO | WO-2004/058944 A2 | 7/2004 |
| WO | WO-2004/097006 A1 | 11/2004 |
| WO | WO-2005/042569 A1 | 5/2005 |
| WO | WO 2005/062967 | 7/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008/057240 A2 | 5/2008 |
| WO | WO-2008/068879 A1 | 6/2008 |
| WO | WO-2008/087184 A1 | 7/2008 |
| WO | WO-2008/121616 A2 | 10/2008 |
| WO | WO-2008/135498 A2 | 11/2008 |
| WO | WO-2009/027041 A1 | 1/2009 |
| WO | WO 2009/017491 | 2/2009 |
| WO | WO-2009/023562 A2 | 2/2009 |
| WO | WO-2009/058769 A1 | 5/2009 |
| WO | WO-2009/073569 A2 | 6/2009 |
| WO | WO 2010/048183 | 10/2009 |
| WO | WO-2009/135656 A1 | 11/2009 |
| WO | WO-2010/036443 A1 | 4/2010 |
| WO | WO-2010/043703 A1 | 4/2010 |
| WO | WO-2010/122460 A1 | 10/2010 |
| WO | WO-2010/127069 A1 | 11/2010 |
| WO | WO-2010/129469 A1 | 11/2010 |
| WO | WO-2011/005773 A2 | 1/2011 |
| WO | WO-2011/009623 A1 | 1/2011 |
| WO | WO-2011/015926 A1 | 2/2011 |
| WO | WO-2011/019619 A1 | 2/2011 |
| WO | WO-2011/024025 A1 | 3/2011 |
| WO | WO-2011/044180 A1 | 4/2011 |
| WO | WO-2011/069056 A2 | 6/2011 |
| WO | WO-2011/073235 A1 | 6/2011 |
| WO | WO-2011/098526 A1 | 8/2011 |
| WO | WO-2011/110598 A1 | 9/2011 |
| WO | WO-2011/127322 A1 | 10/2011 |
| WO | WO-2011/133886 A2 | 10/2011 |

(56) References Cited

FOREIGN PATENT DOCUMENTS

| WO | WO-2011/134919 A2 | 11/2011 |
|---|---|---|
| WO | WO-2011/134920 A1 | 11/2011 |
| WO | WO-2012019160 A1 | 2/2012 |
| WO | WO-2012030512 A1 | 3/2012 |
| WO | WO 2012/046255 | 4/2012 |
| WO | WO-2012/051147 A1 | 4/2012 |
| WO | WO-2012050175 A1 | 4/2012 |
| WO | WO-2012/062810 A2 | 5/2012 |
| WO | WO-2012/065072 A2 | 5/2012 |
| WO | WO-2012/120500 A2 | 9/2012 |
| WO | WO-2012/140138 A1 | 10/2012 |
| WO | WO-2012/145682 A1 | 10/2012 |
| WO | WO-2012/147048 A2 | 11/2012 |
| WO | WO-2012/147053 A1 | 11/2012 |
| WO | WO-2012/149197 A2 | 11/2012 |
| WO | WO-2012/158551 A1 | 11/2012 |
| WO | WO-2013/006461 A1 | 1/2013 |
| WO | WO-2013/006479 A2 | 1/2013 |
| WO | WO-2013/009648 A2 | 1/2013 |
| WO | WO-2013/011076 A2 | 1/2013 |
| WO | WO-2013/013013 A2 | 1/2013 |
| WO | WO-2013/158273 A1 | 10/2013 |
| WO | WO-2013/158275 A1 | 10/2013 |
| WO | WO-2013/158279 A1 | 10/2013 |
| WO | WO 2013/164837 | 11/2013 |
| WO | WO-2013/176754 A1 | 11/2013 |
| WO | WO-2013/177115 A2 | 11/2013 |
| WO | WO-2013/177118 A2 | 11/2013 |
| WO | WO-2013/181585 A2 | 12/2013 |
| WO | WO 2013/186230 | 12/2013 |
| WO | WO 2014/039903 | 3/2014 |
| WO | WO 2014/099636 | 6/2014 |
| WO | WO 2014/207763 | 12/2014 |
| WO | WO 2015/004679 A1 | 1/2015 |
| WO | WO 2015/007912 | 1/2015 |

OTHER PUBLICATIONS

"Memorandum in Support of Centocor's Motion for Summary Judgment No. 2 that all Asserted Claims are Invalid for Lack of Enablement", dated Aug. 1, 2013 and submitted by defendant in Civil Action No. 09-40089-FDS, 22 pages.

"Memorandum in Support of Centocor's Motion for Summary Judgment No. 4 that Claims Encompassing Non-recombinant Human Antibodies are Invalid for Failing to Meet the Requirements of 35 U.S.C. §112", dated Aug. 1, 2013 and submitted by defendant in Civil Action No. 09-40089-FDS, 21 pages.

"Memorandum in Support of Centocor's Motion No. 3 for Summary Judgment that the 394 and 031 Patents are Invalid for Under 35 U.S.C. §102(f) for Failing to Name the Proper Inventors", dated Aug. 1, 2013 and submitted by defendant in Civil Action No. 09-40089-FDS,13 pages.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.

"Plaintiffs' Memorandum in Support of Their Motion for Partial Summary Judgment", dated Aug. 1, 2013 and submitted by plaintiff in Civil Action No. 09-40089-FDS, 49 pages.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams, A.E. et al. "Aggressive cutaneous T-cell lymphomas after TNFα blockade". J. Am. Acad. Dermatol Oct. 2004;51 :660-2.

Alfaro, J.F. et al. "Chemo-Enzymatic Detection of Protein Isoaspartate Using Protein Isoaspartate Methyltransferase and Hydrazine Trapping" Anal. Chem. 2008, 80, 3882-3889.

Altamirano, C., et al., "Strategies for fed batch cultivation of t-PA producing CHO cells: substitution of glucose and glutamine and rational design of culture medium", *J. Biotechn*. 110:171-179, 2004.

Andersen, D.C. & Goochee C.F., The effect of cell-culture conditions on the oligosaccharide structures of secreted glycoproteins, Current Opinion in Biotechnology 1994, 5:546-549.

Anonymous, "SACHEM Displacement Chromatography," Aug. 29, 2012, Retrieved from the internet: <http://www.displacementchromatography.com>, retrieved on Jul. 30, 2014, pp. 1-12.

Antes, B. et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Averginos, Gab '04 Abstracts—GE Healthcare Life Sciences, "HUMIRA manufacturing: challenges and the path taken", France, Oct. 3-5, 2004, published 2005, pp. 14-16.

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Barbuto, J. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).

Barnes, L.M. et al., "Stability of Protein Production from Recombinant Mammalian Cells," Biotechnology and Bioengineering, 81 :6, Mar. 20, 2003, pp. 631-639.

BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pdf>), (last accessed Jan. 8, 2015), 4 pages.

Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).

Biblia, T.A. et al., "In Pursuit of the Optimal Fed-Batch Process for Monoclonal Antibody Production", Biotechnol. Prog 11(1):1-13, Jan.-Feb. 1995.

Birch, JR. et al., "Antibody production", Adv. Drug Delivery Reviews 58:671-685, 2006.

Blaker, GJ, et al., "The Glucose, Insulin and Glutamine Requirements of Suspension Cultures of HeLa Cells in a Defined Culture Medium", J. Cell Sci. 9:529-537, 1971.

Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).

Bollati-Fogolin M., et al., "Temperature Reduction in Cultures of hGM-CSF-expressing CHO Cells: Effects on Productivity and Product Quantity", Biotechnol. Prog. 21:17-21, 2005.

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.

Boswell et al. "Effects of Charge on Antibody Tissue Distribution and Pharmacokinetics" Bioconjugate Chem.(21) 2153-2163 (2010).

Boyle, P. et al. "A Novel Monoclonal Human IgM Autoantibody which Binds Recombinant Human and Mouse Tumor Necrosis Factor-α" *Cell. Immunol.*, 152:556-68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).

Brekke, O. et al., "Therapeutic Antibodies for Human Diseases at the Dawn of the Twenty-first Century," *Nature*, vol. 2:52-62 (2002).

(56) References Cited

OTHER PUBLICATIONS

Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).
Bruggemann, M., Neuberger, M.S., "Strategies for expressing human antibody repertoires in transgenic mice," *Immunol. Today* 17:391-397 (1996).
Burteau, C.C. et al., Fortification of a Protein-Free Cell Culture Medium With Plant Peptones Improves Cultivation and Producticvity of an Interferon-γ-Producticng Cho Cell Line, In Vitro Cell. Dev. Biol.—Animal 39:291-296, Jul./Aug. 2003.
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al., "Humanization of an anti-p185HER2 antibody for human cancer therapy," *Proc. Nat. Acad. Sci* 89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Charter, Edward A., "A New Process for the Separation and Purification of Egg Yolk; Antibodies," BASc., The University of British Columbia; A Thesis; Apr. 1993, 163 pages.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research,* 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Chung et al., "Utilization of Lysozyme Charge Ladders to Examine the Effects of Protein Surface; Charge Distribution on Binding Affinity in Ion Exchange Systems," Langmuir 26(2): 759-768 (2010).
Chung, C.H. et al., "Cetuximab-Induced Anaphylaxis and IgE Specific for Galactose-α-1, 3-Galactose", *N. Engl. J. Med.,* 358:11, pp. 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences,* vol. 90(3):310-321 (2001).
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," *Crit Care Med,* vol. 24(9):1431-1440 (1996).
Cox, J. et al. "A directory of human germ-line Vκ segments reveals a strong bias in their usage" *Eur. J. Immunol.,* 24(2):827-36 (1994).
Cromwell (GAB'04 Abstracts—GE Healthcare Life Sciences, Franc Oct. 3-5, 2004, pp. 17-18 published 2005).
Crowell, C.K. et al., Amino Acid and Manganese Supplementation Modulates the Glycosylation State of Erythropoietin in a CHO Culture System, Biotechnology and Bioengineering, vol. 96, No. 3, Feb. 15, 2007, pp. 538-549.

Cygnus Technologies http://www.cyngnustechnologies.com/product_detail/host -cell-protein -antibodies/anti -choh...Anti-CHO HCP (Apr. 18, 2012), 1 page.
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology,* 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita, V.M. et al., "Phosphate feeding improves high-cell-concentration NSO myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", *Immunotechnology,* 1:197-209 (1995).
Doring, E., "Identification and Characterization of a TNFa Antagonist Derived from a Monoclonal Antibody" (1994) *Mol. Immunol.* 31(14): 1059-1067.
Du Y, et al., "Chromatographic analysis of the acidic and basic species of recombinant monoclonal antibodies" mAbs, Sep.-Oct. 2012); 4(5):578-85.
Elliot et al., "Repeated therapy with monoclonal antibody to tumour necrosis factor α (cA2) in patients with rheumatoid arthritis" (1994) *Lancet,* 344:1125-1127.
Elliot, "Treatment of rheumatoid arthritis with chimeric monoclonal antibodies to tumor necrosis factor α" (1993) *Arthritis & Rheumatism,* 36(12):1681-1690.
Ellison, Jay W. et al., "The Nucleotide Sequence of a Human Immunoglobulin Cγ1 Gene," Nucleic Acids Research, vol. 10, No. 13 (1982), 9 pages.
Emery, P. "Adalimumab therapy: Clinical findings and implications for integration into clinical guidelines for rheumatoid arthritis." *Drugs of Today,* 41(3): p. 155-153. (2005).
Erbitux (cetuximab) label, Revised Aug. 2013, 8 pages.
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Ewert et al., "Biophysical Properties of Human Antibody Variable Domains," J. Mol. Biol. 324: 531-;553 (2003).
Exhibit dated Aug. 1, 2013 and cited by defendant in Civil Action No. 09-40089-FDS providing the trial transcript in the matter of *Abbott Laboratories, et al. v. The Mathilda and Terrance Kennedy Institute*, S.D.N.Y., 90 pages.
Exhibit dated Aug. 1, 2013 and cited by defendant in Civil Action No. 09-40089-FDS providing the Jun. 23, 2009 trial transcript of the PM session in the matter of *Centocor, et al. v. Abbott Laboratories*, 50 pages.
Exhibit dated Aug. 1, 2013 and cited by defendant in Civil Action No. 09-40089-FDS providing the Jun. 24, 2009 trial transcript of the AM session in the matter of *Centocor, et al. v. Abbott Laboratories*, E.D. TX., 42 pages.
Exhibit dated Aug. 1, 2013 and cited by defendant in Civil Action No. 09-40089-FDS providing the Sep. 20, 2012 Day 8 trial transcript in the matter of *Abbott v. Centocor Ortho Biotech Inc.,* D. MA., 71 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by plaintiff in Civil Action No. 09-40089-FDS providing Declaration by Jochen Salfeld, dated Jan. 17, 2013, 40 pages.

(56) References Cited

OTHER PUBLICATIONS

FDA Package insert for Adalimumab, http://www.accessdata.fda.gov/drugsatfda_docs/label/2002/adalabb123102LB.htm, accessed on the Internet Feb. 20, 2014, pp. 16 pages.
Feldmann, "Anti-TNF-alpha Therapy of Rheumatoid Arthritis: What Have We Learned?" (2001) *Annu. Rev. Immunol.*, 19:163-196.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Furukawa, Kazuki et al., "Enhancement of productivity of recombinant α-amidating enzyme by low temperature culture", Cytotechnoloqy 31:85-94, 1999.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2, access on the Internet Feb. 20, 2014, http://www.ncbi.nlm.nih.gov/protein/EGW13555.
Genentech unveils production capacity hikes, in-Pharma Technologist.com Jun. 28, 2005, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Goochee, C.F. et al., The oligosaccharides of glycoproteins: Bioprocess factors affecting oligosaccharide structure and their effect on glycoprotein properties, Biotechnology, vol. 9 Dec. 1991, pp. 1347-1355.
Goswami et al., "Developments and Challenges for mAb-Based Therapeutics," *Antibodies*, 2:452-500, 2013.
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Gramer M J. et al. "Modulation of Antibody Galactosylation Through Feeding of Uridine, Manganese Chloride, and Galactose",Biotechnology and Bioengineering, Wiley & Sons, Hoboken, NJ, US,vol. 108, No. 7,Jul. 1, 2011, pp. 1591-1682.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.

Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grünberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine", Biotechnology and Bioengineering, Wiley & Sons, Hoboken, NJ, US, vol. 58, No. 6, Jun. 20, 1998, pp. 642-648.
Harding et al., "Class switching in human immunoglobulin transgenic mice" (1995) *Ann. NY Acad. Sci.*, 764:536-547.
Harlow and Lane, Antibodies A Laboratory Manual, Purification of Antibodies by using a; Deae-matrix (Batch), Storing and Purifying Antibodies; Chapter 8: 302-303 (1988).
Harlow and Lane, Antibodies A Laboratory Manual,; pp. 25, 42, 72, 76, (1988).
Harris, Reed J. et al., "Structural Characterization of a Recombinant CD4-IgG Hybrid Molecule," Eur. J. Biochem. 194:611-620 (1990).
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hills, A.E., Metabolic control of Recombinant Monoclonal Antibody N-Glycosylation in GS-NS0 Cells, Biotechnology and Bioengineering, vol. 75, No. 2, Oct. 20, 2001, pp. 239-251.
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al., "Optimal and consistent protein glycosylation in mammalian cell culture", Glycobiology; (2009), 19(9):936-949.
Hossler et al.; "Improvement of mammalian cell culture performance through surfactant enabled concentrated feed media"; Biotechnology Progress; 29(4):1023-1033 (2013).

(56) References Cited

OTHER PUBLICATIONS

Huang et al. "Effects of anti-TNF monoclonal antibody infusion in patients with hairy cell leukaemia" (1992) *Br. J. Haematol.*, 81(2):231-234.
Humira (adalimumab) label, *Revised* Sep. 2013, 87 pages.
Humira (adalimumab) prescribing information, Dec. 20, 2002, pp. 1-16.
Huse, "Generation of a large combinatorial library of the immunoglobulin repertoire in phage lambda" (1989) *Science*, 246:1275-81.
HyClone CDM4CHO Media—Fisher Scientific http://www.fishersci.com/ecomm/servlet/fsproductdetail?storeId=10652&productId=1196 . . . Accessed on the Internet Jan. 22, 2015, 1 page.
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011, 5 pages.
International Preliminary Report on Patentability for Application No. PCT/US2013/031389, Dated Oct. 30, 2014, 9 pages.
International Preliminary Report on Patentability for Application No. PCT/US2013/031485, Dated Oct. 30, 2014, 7 pages.
International Preliminary Report on Patentability for Application No. PCT/US2013/041954, dated Dec. 4, 2014, 14 pages.
International Preliminary Report on Patentability for Application No. PCT/US2013/031352, Dated Dec. 4, 2013, 9 pages.
International Preliminary Report on Patentability for Application No. PCT/US2011/060388, dated May 2013, 9 pages.
International Preliminary Report on Patentability for Application No. PCT/US2013/031681, dated Oct. 21, 2014, pp. 1-8.
International Search Report and Written Opinion for Application No. PCT/US2013/031380, dated Feb. 5, 2014, 20 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Preliminary Report on Patentability for Application No. PCT/US2013/041958, dated Nov. 25, 2014, 12 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013.
Statement on a Nonproprietary Name Adopted by the Usan Council: Adalimumab (2001) 1 page.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report from PCT/US2014/024256 dated Jul. 30, 2014, pp. 1-15.
Invitation to Pay Additional Fees for International Application No. PCT/US2013/065749, Dated May 27, 2014, pp. 1-8.
Invitation to Pay Additional Fees for International Application No. PCT/US2013/031380, Dated Nov. 28, 2013, 5 pages.
Invitation to Pay Additional Fees for International Application No. PCT/US2014/026606, Dated Jul. 8, 2014, pp. 1-8.
Jakobovits, A., "Production of fully human antibodies by transgenic mice" (1995) *Curr. Op. Biotechnol.*, 6:561-566.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jespers, "Guiding the Selection of Human Antibodies from Phage Display Repertoires to a Single Epitope of an Antigen" (1994) *Bio/Technology*, 12:899-903.
Johnson et al., "Characterization of cathepsin L secreted by Sf21 insect cells", Archives of Biochemistry and Biophysics (2005), 444:7-14.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "TNF-αantagonists beyond approved indications: stories of success and prospects for the future", Q J Med (2010) 103:917-928.
Kaschak et al: "Characterization of the basic charge variants of a human IgGI: Effect of copper concentration in cell culture media", MABS, vol. 3, No. 6, Nov. 1, 2011, pp. 577-583.
Kempeni, "Update on D2E7: a fully human anti-tumour necrosis factor-alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatoqraphy, 266:3-21 (1983).
Kwon et al., "Production of lactic acid by *Lactobacillus rhamnosus* with vitamin-supplemented soybean hydrolysate", Enzyme Microb Technol. (2000), 26:209-215.
Lerner, "Antibodies without immunization" (1992) *Science*, 258:1313-1314.
Leusch, "Failure to demonstrate TNFα-specific autoantibodies in human sera by ELISA and Western blot" (1991) *J. Immunol. Methods*, 139:145-47.
Lewis, "Use of alanine scanning mutagenesis to improve the affinity of an anti gp120 (HIV) antibody" (1994) *J. Cell. Biochem.*, 18D:215.

(56) References Cited

OTHER PUBLICATIONS

Li et al., "Cell Culture Processes for Monoclonal Antibody Production," mAbs, 2:5, 466-477, Sep./Oct. 2010.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1H Expressed in Different Cell Lines and Grown Under Different Culture Conditions", *Glycobiology*, 5(8):813-822 (1995).
Liu et al., "Recovery and purification process development for monoclonal antibody production," MABS (2010) 2(5):480-499.
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.
Low et al., "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract ( 1996) *Cambridge University*, 1 page.
Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Luo et al., "Understanding of C-terminal lysine variants in antibody production using mammalian cells" Abstract of papers, ACS, Anaheim, CA, US, Mar. 2011, 1 page.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress."
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) *J. Mol. Biol.*, 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*Proteins: Structure, Function and Genetics*, 25:130-133.
Martinelle, K. et al., "Effect of different cell culture medium surfactants on cell growth and viability", Cells and Culture, Proceedings of the 20th ESACT Meeting v4 819-822, Jun. 17-20, 2007.
McAtee et al., "Isolation of monoclonal antibody charge variants by displacement chromatography," Current Protocols in Protein Science, 8.10-8.10.13, 2012.
Medynski, "Phage Display: All Dressed Up and Ready to Role" (1994) *Bio/Technology*, 12:1134-1136.

Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Möller, Monoclonal antibodies to human tumor necrosis factor α: in vitro and vivo application (1990) *Cytokine*, 2(3):162-69.
Moore, A., et al., "Effects of temperature shift on cell cycle, apoptosis and nucleotide pools in CHO cell batch cultures", Cytotechnology, 23:47-54, 1997.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Oh, D-K. et al., "Increased erythritol production in fed-batch cultures of *Torula* sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Pacis, et al.: "Effects of cell culture conditions on antibody N-linked glycosylation-what affect high mannose 5 glycoform", Biotechnology and Bioengineering vol. 108, No. 10 Oct. 2011, pp. 2348-2358.
Parekh, R.B. et al., Association of rheumatoid arthritis and primary osteoarthritis with changes in the glycosylation pattern of total serum IgG, Nature 316, 452-457 (Aug. 1, 1985).
Parekh, R.B. et al., N-glycosylation and the production of recombinant glycoproteins, TIBTECH May 1989 vol. 117-122.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Perchiacca et al., "Aggregation-resistance domain antibodies engineered with charged mutations; near the edges of the complementarity-determining regions," Protein Engineering Design & Selection, 25: 10 (591-601) 2012.
Perchiacca, J.M et. al. "Engineering Aggregation—Resistant Antibodies"; Annu. Rev. Chem. Biomol. Eng. 2012.3:263-2.
Pietersz et al., "In vitro and in vivo Antitumor Activity of a Chimeric anti-CD19 Antibody", *Cancer lmmunol. Immunother.*, 41:53-60 (1995).
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Potter et al., "Antibody Production in the Baculovirus Expression System", *Intern. Rev. Immunol.*, 10:103-112 (1993).

(56) References Cited

OTHER PUBLICATIONS

Poul et al., "Design of Cassette Baculovirus Vectors for the Production of Therapeutic Antibodies in Insect Cells", *Immunotechnology*, 1:189-196 (1995).
Protein Isoelectric Point, The pi Calculator available at the Sequence Manipulation Suite (see <http://bioinformatics.org/sms2/protein_iep.html>), downloaded Feb. 25, 2014, 2 page).
Protein Molecular Weight, MW Calculator available at the Sequence Manipulation Suite (see http://bioinformatics.org/sms2/protein_mw.html) downloaded Feb. 25, 2014, 2 pages.
Queen, C., "A humanized antibody that binds to the interleukin 2 receptor" (1989) *Proc. Natl. Acad. Sci. USA*, 86(24):10029-10033.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International.*, 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Rheinwald J.G., et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.
Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.
Satoh, M. et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Schiestl et al. "Acceptable changes in quality attributes of glycosylated biopharmaceuticals" Nature Biotechnology, 29(4), 310-312 (2011).
Schwieterman, "Immunosuppression in Combination with Monoclonal Antibodies" in Biologic Agents in Autoimmune Disease (Mar. 2-4, 1995), 9 pages.
Senczuk et al. "Hydrophobic interaction chromatography in dual salt system increases protein binding capacity" Biotechnology and Bioengineering, 103(5), 930-935 (2009).
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shen, Amy Y. et al., "Recombinant DNA Technology and Cell Line Development," from "Cell Culture Technology for Pharmaceutical and Cell-Based Therapies," CRC Press, 1995, 15-40.
Shih, "Effects of Anions on the Deamidation of Soy Protein". Journal of Food Science. 1991, 56: 452-454.
Shukla et al., "Host cell protein clearance during protein A chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sigma Catalog "RPMI1640" (last accessed Jan. 22, 2015), 3 pages.
Sigma MSDS for RMPI1640 (last accessed Jan. 22, 2015), 6 pages.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sundaram et al., "An innovative approach for the characterization of the isoforms of a monoclonal antibody product," Mabs, 3(6):505-512, 2011.
Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.
Tan et al., "Expression and purification of a secreted functional mouse/human chimaeric antibody against bacterial endotoxin in baculovirus-infected insect cells", Biotechnol. Appl. Biochem. (1999), 30:59-64.
Taylor et al.,"Human immunoglobulin transgenes undergo rearrangement, somatic mutation and class switching in mice that lack endogenous IgM" (1994) *Int. Immunol.*, 6:579-591.
Teichmann, S. Declaration dated Dec. 17, 2010 from opposition proceedings in EP 0929578, 6 pages.
TESS database "HYCLONE" Trademark #85769283. Filing date Sep. 30, 2012. Live mark. Last accessed Jan. 21, 2015.
TESS database "HYCLONE" Trademark #76244963. Filing date Apr. 23, 2001. Live mark. Last accessed Jan. 21, 2015.

(56) References Cited

OTHER PUBLICATIONS

Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action", 4 pages.
Thompson, "Affinity maturation of a high-affinity human monoclonal antibody against the third hypervariable loop of human immunodeficiency virus: use of phage display to improve affinity and broaden strain reactivity" (1996) J. Mol. Biol., 256(1):77-88.
Thorp, K.M. et al., "Tumour Necrosis Factor Induction of ELAM-1 and ICAM-1 on Human Umbilical Vein Endothelial Cells—Analysis of Tumour Necrosis Factor Receptor Interaction" ( 1992) Cytokine, 4(4): 313-319.
Tomiya et al., "Comparing N-glycan processing in mammalian cell lines to native and engineered; lepidopteran insect cell lines," Glycoconjuqate Journal 21 :343-360 (2004).
Tomlinson, "The repertoire of human germline VH sequences reveals about fifty groups of VH segments with different hypervariable loops" (1992) J. Mol. Biol., 227:776-98.
Tomlinson, "The structural repertoire of the human Vk domain" (1995) The EMBO J., 14(18):4628-38.
Tracey, "Tumor necrosis factor: A pleiotropic cytokine and therapeutic target" (1994) Annu. Rev. Med., 45:491-503.
Tsuchiyama et al., "Comparison of anti-TNF alpha autoantibodies in plasma and from EBV transformed lymphocytes of autoimmune and normal individuals" (1995) Hum. Antibod. Hybridomas, 6(2):73-76.
United States Food and Drug Administration (FDA) Biological Licensing Application File No. 125057 (Adalimumab) (Dec. 31, 2002) (Last Accessed Mar. 11, 2015 at <http://www.fda.gov/Drugs/DevelopmentApprovalProcess/uHowDrugsareDevelopedandApproved/ApprovalApplications/TherapeuticBiologicApplications/ucm080610.htm>), 1 page.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", J. Biol. Chem., 285:16012-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) Clin. Exp. Immunol., 100:21-25.
Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vassalli, P., "The Pathophysiology of Tumor Necrosis Factors", Annu. Rev. Immunol. 1992, 10: 411-52.
Vaughan, "Human antibodies by design" (1998) Nature Biotechnology, 16:535-539.
Wagner et al., "Antibodies generated from human immunoglobulin miniloci in transgenic mice" (1994) Nucl. Acids Res. 22:1389-1393.
Wagner et al., "The diversity of antigen-specific monoclonal antibodies from transgenic mice bearing human immunoglobulin gene miniloci" (1994) Eur. J. Immunol., 24:2672-2681.
Ward, "Binding activities of a repertoire of single immunoglobulin variable domains secreted from Escherichia coli" (1989) Nature, 341 :544-546.
Wedemayer et al., "Structural insights into the evolution of an antibody combining site" (1997) Science, 276:1665-1669.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) Immunol. Today, 14(6):243-246.
Winter, "Making antibodies by phage display technology" (1994) Annu. Rev. Immunol., 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Yigzaw et al., "Exploitation of the adsorptive properties of depth filters for host cell protein removal during monoclonal antibody purification," Biotechnology Progress, (2006) 22(1):288-296.
Yumioka et al., "Screening of effective column rinse solvent for Protein-A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) FASEB J., 10:1227-1232.
Lo, T.W. et al., Binding and modification of proteins by methylglyoxal under physiological conditions. A kinetic and mechanistic study with N alpha-acetylarginine, N alpha-acetylcysteine, and N alpha-acetyllysine, and bovine serum albumin, Dec. 23, 1994, The Journal of Biological Chemistry, 269, 32299-32305.
Paoli, T. et al., A Study of D-Lactate and Extracellular Methylglyoxal Production in Lactate Re-Utilizing CHO Cultures, Biotechnology and Bioengineering, vol. 107, No. 1, Sep. 1, 2010, pp. 182-189.
Chaplen, F.W.R., et al., Effect of endogenous methylglyoxal on Chinese hamster ovary cells grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chang, T. & Wu, L., Methylglyoxal, oxidative streee, and hypertension, Can. J. Physiol. Pharmacol. 84: 1229-1238 (2006).
Kingkeohoi, S. & Chaplen, F.W.R., Analysis of methylglyoxal metabolism in CHO cells grown in culture, Cytotechnology (2005) 48:1-13.
Roy, B.M., et al., Toxic concentrations of exogenously supplied methylglyoxal in hybridoma cell culture, Cytotechnology (2004) 46:97-107.
Ahmed, M. U.et al.; $N^\varepsilon$-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043, 260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Biastoff, S.; et al.; Colorimetric Activity Measurement of a Recombinant Putrescine N-Methyltransferase from Datura stramonium; Planta Med. 2006, 72, 1136.

(56) References Cited

OTHER PUBLICATIONS

Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77, 6004-6011.
Dai, S.; An Integrated Proteomic Analysis of Major Isoaspartyl-Containing Proteins in the Urine of Wild Type and Protein L1soaspartate O-Methyltransferase-Deficient Mice; Anal. Chem. 2013, 85, 2423-2430.
Dobo, A. & Kaltashov, I. A.; Detection of Multiple Protein Conformational Ensembles in Solution via Deconvolution of Charge-State Distributions in ESI MS; Anal. Chem. 2001, 73, 4763-4773.
Gauthier, M. A.& Klok, H.-A. Arginine-Specific Modification of Proteins with Polyethylene Glycol Biomacromolecules; 2011, 12, 482-493.
Hipkiss, A.; Can the beneficial effects of methionine restriction in rats be explained in part by decreased methylglyoxal generation resulting from suppressed carbohydrate metabolism?; Biogerontology 2012, 13, 633-636.
Jack, M.; Wright, D.; The Role of Advanced Glycation Endproducts and Glyoxalase I in Diabetic Peripheral Sensory Neuropathy; Transl. Res. 2012, 159, 355-365.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82, 7485-7491.
Ouellette, D.; Studies in serum support rapid formation of disulfide bond between unpaired cysteine residues in the VH domain of an immunoglobulin G1 molecule; Anal. Biochem. 2010, 397, 37.
Perkins, M.; et. Al. Determination of the Origin of Charge Heterogeneity in a Murine Monoclonal Antibody; M. Pharm. Res. 2000, 17, 1110-1117.
Rabbani, N.; Thornalley, P. J.; Glyoxalase in diabetes, obesity and related disorders; Semin. Cell Dev. Biol. 2011, 22, 309-317.
Saxena, R. K. et al.; Microbial production and applications of 1,2-propanediol; Indian J. Microbiol. 2010, 50, 2-11.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Walsh, G.; Post-Translational Modification of Protein Biopharmaceuticals; Wiley: Weinheim, Germany, 2009, pp. 1-14.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Zang, T.; et al.; Chemical Methods for the Detection of Protein N-Homocysteinylation via Selective Reactions with Aldehydes; Anal. Chem. 2009, 81, 9065-9071.
Zhang, T.; Identification and Characterization of Buried Unpaired Cysteines in a Recombinant Monoclonal IgG1 Antibody; Anal. Chem. 2012, 84, 7112-7123.
Zhao, G.; Chemical Synthesis of S-Ribosyl-L-homocysteine and Activity Assay as a LuxS Substrate; Bioorg. Med. Chem. Lett. 2003, 13, 3897-3900.
Zhou, Z. et al.; An Antibody-Catalyzed Allylic Sulfoxide-Sulfenate Rearrangement; J. Org. Chem. 1999, 64, 8334-8341.
Zhou, Z. S. et al. An Antibody-Catalyzed Selenoxide Elimination; J. Am. Chem. Soc. 1997, 119, 3623-3624.
Awdeh, Z.L., A.R. Williamson, and B.A. Askonas, *One cell-one immunoglobulin. Origin of limited heterogeneity of myeloma proteins.* Biochem J, 1970. 116(2): p. 241-8.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.
Cordoba, A.J., et al., Non-enzymatic hinge region fragmentation of antibodies in solution. Journal of Chromatography B, 2005. 818(2): p. 115-121.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Harris, R.J., et al., *Identification of multiple sources of charge heterogeneity in a recombinant antibody.* Journal of Chromatography B: Biomedical Sciences and Applications, 2001. 752(2): p. 233-245.
Harris, R.J., Processing of C-terminal lysine and arginine residues of proteins isolated from mammalian cell culture, Journal of Chromatography A, 705 (1995) 129-134.
Huang, L., et al., *In Vivo Deamidation Characterization of Monoclonal Antibody by LC/MS/MS.* Analytical Chemistry, 2005. 77(5): p. 1432-1439.
Jakubowski, H., Protein N-homocysteinylation: implications for atherosclerosis. Biomedicine & Pharmacotherapy, 2001. 55(8): p. 443-447.
Jefferis, R., *Glycosylation of Recombinant Antibody Therapeutics.* Biotechnology Progress, 2005. 21(1): p. 11-16.
Johnson, K.A., et al., Cation exchange HPLC and mass spectrometry reveal C-terminal amidation of an IgG1 heavy chain. Analytical Biochemistry, 2007. 360(1): p. 75-83.
Liu, H., et al., *Heterogeneity of monoclonal antibodies.* Journal of Pharmaceutical Sciences, 2008. 97(7): p. 2426-2447.
Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Manning, M., et al., *Stability of Protein Pharmaceuticals: An Update.* Pharmaceutical Research, 2010. 27(4): p. 544-575.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Parekh, R.B., et al., Association of rheumatoid arthritis and primary osteoarthritis with changes in the glycosylation pattern of total serum IgG. Nature, 1985. 316(6027): p. 452-7.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Reed J, H., Processing of C-terminal lysine and arginine residues of proteins isolated from mammalian cell culture. Journal of Chromatography A, 1995. 705(1): p. 129-134.
Ren, D., et al., Reversed-phase liquid chromatography—mass spectrometry of site-specific chemical modifications in intact immunoglobulin molecules and their fragments. Journal of Chromatography A, 2008. 1179(2): p. 198-204.

(56) References Cited

OTHER PUBLICATIONS

Vasilli, P., Annu. Rev. Immunol. 10:411-452 (1992); and Tracey, K. J. and Cerami, A. Annu. Rev. Med. 45:491-503 (1994).

Vlasak, J. & Ionescu, R., *Heterogeneity of Monoclonal Antibodies Revealed by Charge-Sensitive Methods.* Current Pharmaceutical Biotechnology, 2008. 9(6): p. 468-481.

Xiang, T., Chumsae, C. & Liu, H., Localization and Quantitation of Free Sulfhydryl in Recombinant Monoclonal Antibodies by Differential Labeling with $^{12}C$ and $^{13}C$ Iodoacetic Acid and LC-MS Analysis. Analytical Chemistry, 2009. 81(19): p. 8101-8108.

Zhang, B., et al., Unveiling a Glycation Hot Spot in a Recombinant Humanized Monoclonal Antibody. Analytical Chemistry, 2008. 80(7): p. 2379-2390.

Zhang, W. and Czupryn, M.J., Free Sulfhydryl in Recombinant Monoclonal Antibodies. Biotechnology Progress, 2002. 18(3): p. 509-513.

PCT/US2013/069702 International Search Report & Written Opinion mailed Jan. 31, 2014, 13 pages.

Williams, A. et al., Ion-Exchange Chromatography, Oct. 1998, Supplement 44, pp. 10-10-1-10-10-30.

Oya, T. et al. Methylglyoxal Modification of Protein: Chemical and Immunochemical Characterization of Methylglyoxal-Arginine Adducts. J. Biol Chem. Jun. 25, 1999; vol. 274, No. 26, pp. 18492-19502.

Yuk, I.H. et al., Controlling Glycation of Recombinant Antibody in Fed Batch Cell Cultures, Nov. 2011, Biotechnology and Bioengineering, vol. 108, No. 11 pp. 2600-2610.

Chaplen FW, Fahl WE, Cameron DC. Evidence of high levels of methylglyoxal in cultured Chinese hamster ovary cells. Proc Natl Acad Sci U SA. May 12, 1998;95(1 0):5533-8.

Rudikoff et al. Single amino acid substitution altering antigen-binding specificity. Proc Natl Acad Sci U S A. Mar. 1982;79(6):1979-83.

MacCallum et al. Antibody-antigen interactions: contact analysis and binding site topography. J Mol Biol. Oct. 11, 1996; 262(5):732-45.

A Guide to Serum-Free Cell Culture [online], Oct. 10, 2008 [retrieved Apr. 27, 2014]. Retrieved from Internet Archive Wayback Machine: https://web.archive.org/web/20081010051108/http://tools.invitrogen.com/content/sfs/brochures/SpecialtySFMediaforCC.pdf.

U.S. Appl. No. 14/078,181, Office Action mailed May 7, 2015, 17 pages.

Gao, Y & Wang, Y., Site-Selective Modifications of Arginine Residues in Human Hemoglobin Induced by Methylgloxal, Biochemistry Dec. 2006, 45, pp. 15654-15660.

Babcock, J., et al., "Partial Replacement of Chemically Defined Media with Plant-Derived Protein Hydrolysis," International BioPharm 23(6): 6 pages, Advanstar Publication, United States (2010).

Bandyopadhyay S., et al., "Physicochemical and functional characterization of a biosimilar adalimumab ZRC-3197," Biosimilars:5, pp. 1-18 (2015).

Brock, J.W.C., et al., "Detection and identification of arginine modifications on methylglyoxal-modified ribonuclease by mass spectrometric analysis," J. Mass Spectrom 42:89-100, John Wiley & Sons, Ltd., United States (2007).

Dionex Application Note 125, "Monitoring Protein Deamidation by Cation-Exchange Chromatography," pp. 1-7, Dionex Corporation (2009).

Drew, B., et al., "The Effects of Media Formulations on the Biochemical Profile of IgG Expressed in Sp2/0 Cells as Measured by Cation Exchange HPLC," Poster #1115, European Society of Animal Cell Technology Meeting (ESACT), https://www.sigmaaldrich.com/content/dam/signma-aldrich/docs/SAFC/Posters/1/sp2-0-cells-as-measured-by-cation-exchange-hplc.pdf (2007).

Fahrner, R.L., et al., "Industrial purification of pharmaceutical antibodies: development, operation, and validation of chromatography processes," Biotechnology and Genetic Engineering Reviews, 18, 2001, pp. 301-327.

Gagnon, P., "Polishing methods for monoclonal IgG purification" Chapter 17, Taylor & Francis Group, LLC, pp. 491-505, 2007.

Grosvenor, S., "A New Era in Cell Culture Media Development," International BioPharm 25(7): 7 pages, Advanstar Publication, United States (2012).

International Preliminary Report on Patentability for Application No. PCT/US2013/031365, Mailed Mar. 12, 2015, 9 pages.

Muller-Spath, T. et al., "Chromatographic Separation of Three Monoclonal Antibody Variants Using Multicolumn Countercurrent Solvent Gradient Purification (MCSGP)," Biotechnology and Bioengineering 100(6):1166-1177, Wiley Periodicals, Inc., United States (2008).

Rau, R., "Adalimumab (a fully human anti-tumour necrosis factor alpha monoclonal antibody) in the treatment of active rheumatoid arthritis: the initial results of five trials," Ann Rheum Dis, 61 (Suppl II): ii70-ii73 (2002).

Sargent (pp. 1-3, Internet Archive captured Aug. 28, 2013, http://cellculturedish.com/2012/01/cho-cells-the-top-expressionsystem-of-best-selling-biologic-drugs/).

Shubert, S. and Freitag, R., "Comparison of ceramic hydroxy- and fluoroapatite versus Protein A/G-based resins in the isolation of a recombinant human antibody from cell culture supernatant" J. Chromatography A 1142:106-113, Elsevier B.V., Netherlands (2007).

Supplementary European Search Report and European Search Opinion for EP Application No. 13 87 7986, dated Aug. 4, 2015.

Wang, T., et al., "Exploring Post-translational Arginine Modification Using Chemically Synthesized Methylglyoxal Hydroimidazolones,"Journal of the American Chemical Society 134:8958-8967, American Chemical Society, United States (2012).

U.S. Appl. No. 14/559,346, Office Action mailed Jun. 1, 2015, 20 pages.

International Preliminary Report on Patentability for International Application No. PCT/US2013/069702, The International Bureau of WIPO, Switzerland, issued Sep. 24, 2015, 9 pages.

\* cited by examiner

Fig. 9

|  | ka (1/Ms) | kd (1/s) | KD (M) |
|---|---|---|---|
| 0Lys Run1 | 1.85E+06 | 1.13E-04 | 6.10E-11 |
| 0Lys Run2 | 1.90E+06 | 1.04E-04 | 5.49E-11 |
| 0Lys Run3 | 1.75E+06 | 1.04E-04 | 5.96E-11 |
| Average | 1.83E+06 | 1.07E-04 | 5.85E-11 |
| Peak 1 Run1 | 1.46E+06 | 2.67E-04 | 1.83E-10 |
| Peak 1 Run2 | 1.56E+06 | 2.52E-04 | 1.61E-10 |
| Peak 1 Run3 | 1.53E+06 | 2.53E-04 | 1.66E-10 |
| Average | 1.52E+06 | 2.57E-04 | 1.70E-10 |

SEQUENCE LISTING

```
<160> NUMBER OF SEQ ID NOS: 15

<210> SEQ ID NO 1
<211> LENGTH: 214
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210

<210> SEQ ID NO 2
<211> LENGTH: 451
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 3
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is hydroimidazolone, which is an Arginine
      residue modified by methylglyoxal (MGO).

<400> SEQUENCE: 3

Ala Ser Gln Gly Ile Xaa Asn Tyr Leu Ala Trp Tyr Gln Gln Lys Pro
1               5                   10                  15

Gly Lys

<210> SEQ ID NO 4
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is hydroxylimidine, which is an Arginine
      residue modified by methylglyoxal (MGO).

<400> SEQUENCE: 4

Ala Ser Gln Gly Ile Xaa Asn Tyr Leu Ala Trp Tyr Gln Gln Lys Pro
1               5                   10                  15

Gly Lys

<210> SEQ ID NO 5
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Xaa is hydroxylimidine or hydroimidazolone,
      which are two isoforms of Arginine residue modified by
      methylglyoxal (MGO).

<400> SEQUENCE: 5

Glu Pro Gln Val Tyr Thr Leu Pro Pro Ser Xaa Asp Glu Leu Thr Lys
```

<210> SEQ ID NO 6
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(16)
<223> OTHER INFORMATION: Xaa is hydroxylimidine or hydroimidazolone, which are two isoforms of Arginine residue modified by methylglyoxal (MGO).

<400> SEQUENCE: 6

Glu Val Gln Leu Val Glu Ser Gly Gly Gly Leu Val Gln Pro Gly Xaa
1               5                   10                  15

Ser Leu Arg

<210> SEQ ID NO 7
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(18)
<223> OTHER INFORMATION: Xaa is hydroxylimidine or hydroimidazolone, which are two isoforms of Arginine residue modified by methylglyoxal (MGO).

<400> SEQUENCE: 7

Asp Ile Gln Met Thr Gln Ser Pro Ser Ser Leu Ser Ala Ser Val Gly
1               5                   10                  15

Asp Xaa Val Thr Ile Thr Cys Arg
            20

<210> SEQ ID NO 8
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is hydroxylimidine or hydroimidazolone, which are two isoforms of Arginine residue modified by methylglyoxal (MGO).

<400> SEQUENCE: 8

Tyr Asn Xaa Ala Pro Tyr Thr Phe Gly Gln Gly Thr Lys
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is hydroxylimidine or hydroimidazolone, which are two isoforms of Arginine residue modified by methylglyoxal (MGO).

<400> SEQUENCE: 9

```
Tyr Asn Xaa Ala Pro Tyr Thr Phe Gly Gln Gly Thr Lys Val Glu Ile
1               5                   10                  15

Lys

<210> SEQ ID NO 10
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is hydroxylimidine or hydroimidazolone,
      which are two isoforms of Arginine residue modified by
      methylglyoxal (MGO).

<400> SEQUENCE: 10

Ser Leu Xaa Leu Ser Cys Ala Ala Ser Gly Phe Thr Phe Asp Asp Tyr
1               5                   10                  15

Ala Met His Trp Val Arg
            20

<210> SEQ ID NO 11
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is hydroxylimidine or hydroimidazolone,
      which are two isoforms of Arginine residue modified by
      methylglyoxal (MGO).

<400> SEQUENCE: 11

Tyr Asn Xaa Ala Pro Tyr Thr Phe Gly Gln Gly Thr Lys
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is hydroxylimidine or hydroimidazolone,
      which are two isoforms of Arginine residue modified by
      methylglyoxal (MGO).

<400> SEQUENCE: 12

Ser Phe Asn Xaa Gly Glu Cys
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Ala Ser Gln Gly Met Leu Ala Trp Tyr Gln Gln Lys Pro Gly Lys
1               5                   10                  15
```

```
<210> SEQ ID NO 14
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is hydroxylimidine or hydroimidazolone,
      which are two isoforms of Arginine residue modified by
      methylglyoxal (MGO).

<400> SEQUENCE: 14

Ala Ser Gln Gly Ile Xaa Asn Tyr Leu Ala Trp Tyr Gln Gln Lys Pro
1               5                   10                  15

Gly Lys

<210> SEQ ID NO 15
<211> LENGTH: 26
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Xaa is hydroxylimidine or hydroimidazolone,
      which are two isoforms of Arginine residue modified by
      methylglyoxal (MGO).

<400> SEQUENCE: 15

Asp Thr Leu Met Ile Ser Xaa Thr Pro Glu Val Thr Cys Val Val Val
1               5                   10                  15

Asp Val Ser His Glu Asp Pro Glu Val Lys
            20                  25
```

HUMAN ANTIBODIES THAT BIND HUMAN TNF-ALPHA AND METHODS OF PREPARING THE SAME

RELATED APPLICATION

This application is a division of U.S. patent application Ser. No. 14/078,181 filed Nov. 12, 2013, which claims priority to U.S. Provisional Patent Application No. 61/777,883, filed Mar. 12, 2013. Both of the aforementioned applications are incorporated by reference into the present application in their entirety and for all purposes.

SEQUENCE LISTING

This application is accompanied by an electronically submitted sequence listing (Name 3685_005000b_SubSeqListing.txt; Size: 11,977 bytes; and Date of Creation: Jul. 16, 2015).

FIELD OF THE INVENTION

This disclosure relates to antibodies that specifically bind to human TNF-alpha. More particular, Methylglyoxal (MGO)-modified recombinant TNF-alpha antibodies are disclosed. Methods for reducing MGO-modified TNF-alpha antibodies are also provided.

BACKGROUND

Tumor necrosis factor alpha ("TNF-alpha") is a cytokine produced by many cell types such as monocytes and macrophages. See e.g., Old, L. Science 230:630-632 (1985). TNF-alpha plays an important role in many biological processes and has been implicated in the pathophysiology of a variety of other human diseases and disorders, including sepsis, infections, autoimmune diseases, transplant rejection and graft-versus-host disease. See e.g., Vasilli, P., Annu. Rev. Immunol. 10:411-452 (1992); and Tracey, K. J. and Cerami, A. Annu. Rev. Med. 45:491-503 (1994).

In an effort to treat/prevent these diseases, various therapeutic strategies have been designed to inhibit or counteract TNF-alpha activities. U.S. Pat. No. 6,090,382 disclosed human antibodies (e.g., recombinant human antibodies) that specifically bind to human TNF-alpha with high affinity and slow dissociation kinetics. Nucleic acids, vectors and host cells for expressing the recombinant human TNF-alpha antibodies were also disclosed. One example of such recombinant TNF-alpha antibodies is called Adalimumab, which is marketed under the trade name Humira®. The entire contents of U.S. Pat. No. 6,090,382 is hereby incorporated by reference into the present disclosure.

Recombinant biotherapeutics are typically produced by live cells and are inherently more complex as compared to traditional small molecule drug. Various post-translational modifications have been reported as major contributors to heterogeneity in recombinant monoclonal antibodies (References 1-4). Some of these modifications, for example, glycosylation and sialic acid incorporation, may occur during fermentation (References 5-7). Some other modifications, such as oxidation and disulfide bond scrambling, may occur during production, purification and storage.

One example of such modifications is the so-called acidic species (charge variants). Acidic species are observed when recombinant monoclonal antibodies are analyzed by weak-cation exchange chromatography (WCX) (FIG. 1). One major contributing factor is the removal of the C-terminal lysine of the heavy chain by cell-derived carboxypeptidease, reducing the overall positive charge (Reference 8). These variants are commonly referred to as Lys0, Lys1 and Lys2 species, respectively.

C-terminal amidation (Reference 9) is another enzymatic process during fermentation. Another type of variant is caused by spontaneous non-enzymatic transformations, which include the formation of pyruglutamate (Pyro-Glu) from an N-terminal glutamine (Gln) that remove the positive charge of the free N-terminus (Reference 10), and the deamidation of asparagine (Asn) to aspartic (Asp) or isoaspartic acid (isoAsp or isoD) that introduces negatively charged carboxylic acids (References 11 and 12).

Some modifications may shift the retention time of antibody on weak cation exchange chromatography even though they do not alter the formal charges of the antibody molecule. These modifications may exert their effects through perturbation of local charge and conformation. For instance, incomplete glycosylation (Reference 13) or the presence of free sulfhydryl (References 14-16) may shift the retention time of antibody on weak cation exchange chromatography. It is worth noting that some modifications are imparted by metabolites, such as glycation by glucose, methionine oxidation by reactive oxygen species (ROS), cysteinylation by cysteine (Reference 17), and S-homocysteinylation and N-homocysteinylation by homocysteine (References 2, 18-23). Although the mechanisms of many modifications have been reported, these mechanisms cannot fully explained the observed heterogeneity of recombinant monoclonal antibodies on weak cation exchange chromatography.

SUMMARY

This disclosure advances the art by identifying novel species of modified recombinant antibodies that may negatively impact the functionalities of such antibodies. The disclosure also provides methods for reducing the amount of such species without substantially compromising the overall yield of the antibody production.

In one embodiment, two acidic species of the Adalimumab antibody are disclosed which exist when the antibody are expressed in Chinese hamster ovary (CHO) cells cultured in chemically defined media (CDM). Detailed analyses have revealed that several arginine residues in Adalimumab are modified by methylglyoxal (MGO), which is further confirmed by the treatment of native antibody with authentic MGO. The reaction between MGO and arginine result in formation of hydroxylimide and/or hydroimidazolone. The resulting hydroxylimide and hydroimidazolone adducts increase the molecular weight of the antibody by 54 and 72 Daltons, respectively.

In another embodiment, these modifications cause the antibody to elute earlier in the weak cation exchange chromatogram as compared to the elution time of unmodified forms. Consequently, the extent to which an antibody was modified at multiple sites corresponds to the degree of shift in acidity and the elution time. The modification of Adalimumab antibody by MGO is the first reported modification of a recombinant monoclonal antibody by MGO.

In another embodiment, a composition is disclosed which contains a binding protein capable of binding TNF-alpha. In one aspect, the binding protein may contain at least one methylglyoxal (MGO)-susceptible amino acid, and at least a portion of the binding protein may contain one or more MGO-modified amino acids.

In another embodiment, a composition is disclosed which contains a binding protein capable of binding TNF-alpha. In one aspect, the binding protein may contain at least one methylglyoxal (MGO)-susceptible amino acid and the composition may be prepared by substantially removing molecules of the binding protein that contain at least one MGO-modified amino acid. The term "substantially" may mean at least 50%. In another aspect, the term "substantially" may mean at least 60%, 70%, 80%, 90%, or even 100% removal of the molecules that contain at least one MGO-modified amino acid.

For purpose of this disclosure, the term "methylglyoxal (MGO)-susceptible" refers to groups or residues (e.g., arginine) that may react with MGO under appropriate cell culture conditions. List of MGO-susceptible arginines in Adalimumab is shown in Table 1. Examples of MGO-susceptible peptides in Adalimumab are shown in Table 2.

The term "at least a portion of the binding protein" means that although all molecules of the binding protein in the composition are capable of binding TNF-alpha, at least two populations of these molecules exist in the composition, wherein one population contain one or more amino acids that have been modified by MGO, while the other population does not contain amino acids that have been modified by MGO. In another aspect, all molecules of the binding protein may contain one or more amino acids that have been modified by MGO.

In one aspect, the portion of the binding protein that contains at least one MGO-modified amino acid is less than 15%, 14%, 13%, 12%, 11%, 10%, 9%, 8%, 7%, 6%, 5%, 4%, 3%, 2% or 1% of the total amount of the binding protein.

In another embodiment, the binding protein is a human antibody or an antigen-binding portion thereof, wherein the binding protein dissociates from human TNF-alpha with a $K_d$ of $1 \times 10^{-8}$ M or less and a $K_{off}$ rate constant of $1 \times 10^{-3}$ $s^{-1}$ or less, both as determined by surface plasmon resonance. In one aspect, the binding protein neutralizes human TNF-alpha cytotoxicity in a standard in vitro L929 assay with an $IC_{50}$ of $1 \times 10^{-7}$ M or less, described in Example 4 of U.S. Pat. No. 6,090,382. In another aspect, the binding protein is the D2E7 antibody as described in U.S. Pat. No. 6,090,382.

In another embodiment, cell culture parameters may affect the extent of modifications by methylglyoxal (MGO). MGO is a highly reactive metabolite that may be generated from glucose, lipids or other metabolic pathways. In one aspect, cell culture conditions may be modified to decrease the production of MGO thereby reducing modification of the recombinant antibodies by MGO. Taken together, the disclosed findings highlight the impact of cell culture conditions on the critical quality attributes of recombinantly produced antibodies. These findings provide additional parameters for improving manufacturing processes and may prove useful for the quality by design (QbD) approach.

In another embodiment, methods are disclosed for purifying a target protein product from both process and/or product related impurities. Specifically, method for purifying a composition containing a target protein is disclosed. In one aspect, methods are provided for reducing product related charge variants (i.e. acidic and basic species). In another aspect, the method involves contacting the process mixture with an ion (anion or cation) exchange adsorbent in an aqueous salt solution under loading conditions that permit both the target and non-target proteins to bind to the adsorbent and allowing the excess target molecule to pass through the column and subsequently recovering the bound target protein with a wash at the same aqueous salt solution used in the equilibration (i.e. pre-loading) condition.

In another embodiment, a method for purifying a composition containing a target protein is disclosed which may include at least the following steps: (a) loading the composition to a cation exchange adsorbent using a loading buffer, wherein the pH of the loading buffer is lower than the pI of the target protein; (b) washing the cation exchange adsorbent with a washing buffer, wherein the pH of the washing buffer is lower than the pI of the target protein; (c) eluting the cation exchange adsorbent with an elution buffer, said elution buffer being capable of reducing the binding between the target protein and the cation exchange adsorbent; and (d) collecting the eluate, wherein the percentage of the target protein is higher in the eluate than the percentage of the target protein in the composition. In one aspect, the washer buffer and the loading buffer are the same. In another aspect, the conductivity of the elution buffer is higher than the conductivity of the washer buffer. In another aspect, the pH of the elution buffer may be between 5.5 and 9.0, between 6 and 8, or between 6.5 and 8. The conductivity of the elution buffer may be raised by increasing the salt concentration of the elution buffer. The salt concentration of the elution buffer may be between 20 mM NaCl and 200 mM NaCl, between 40 mM NaCl and 160 mM NaCl, or between 60 mM NaCl and 120 mM NaCl.

In another embodiment, a method for purifying a composition containing a target protein is disclosed which may include at least the following steps: (a) loading the composition to an anion exchange adsorbent using a loading buffer, wherein the pH of the loading buffer is lower than the isoelectric point (pI) of the target protein; (b) allowing the majority of the target protein to pass through without binding to the anion exchange adsorbent; (c) collecting the pass-through loading buffer containing said unbound target protein; (d) washing the anion exchange adsorbent with a washing buffer; (e) allowing the target protein bound to the anion exchange adsorbent to disassociate from the anion exchange adsorbent; (f) collecting the washing buffer containing said disassociated target protein. In another aspect, the method may further include a step (g) of pooling the collections from steps (c) and (f) to obtain a purified composition containing the target protein. The percentage of the target protein is higher in the pooled collections than the percentage of the target protein in the original composition.

In one aspect, the loading buffer may contain an anionic agent and a cationic agent, wherein the conductivity and pH of the loading buffer is adjusted by increasing or decreasing the concentration of a cationic agent and maintaining a constant concentration of an anionic agent in the loading buffer. In another aspect, the anionic agent is selected from the group consisting of acetate, citrate, chloride anion, sulphate, phosphate and combinations thereof. In another aspect, the cationic agent is selected from the group consisting of sodium, Tris, tromethalmine, ammonium cation, arginine, and combinations thereof.

In one embodiment, the target protein is a human antibody or an antigen-binding portion thereof that is substantially free from MGO modification. In one aspect, the target protein dissociates from human TNF-alpha with a $K_d$ of $1 \times 10^{-8}$ M or less and a $K_{off}$ rate constant of $1 \times 10^{-3}$ $s^{-1}$ or less, both as determined by surface plasmon resonance. In another aspect, the target protein neutralizes human TNF-alpha cytotoxicity in a standard in vitro L929 assay with an $IC_{50}$ of $1 \times 10^{-7}$ M or less, described in Example 4 of U.S. Pat. No. 6,090,382. In another aspect, the target protein is the D2E7 antibody as described in U.S. Pat. No. 6,090,382.

BRIEF DESCRIPTION OF THE DRAWINGS

FIG. 9 shows Surface Plasmon Resonance (SPR) data for 0 Lys Fraction (Top—0 Lys) and for the MGO enriched fraction (Bottom—Peak 1).

DETAILED DESCRIPTION

Figure 1:
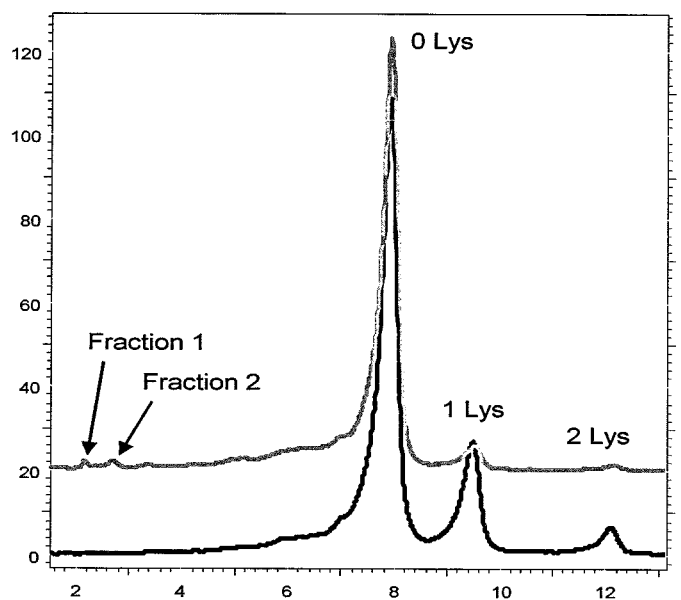
FIG. 1 shows a typical WCX chromatogram of adalimumab after protein A purification.

The instant disclosure identifies novel species of methylglyoxal (MGO)-modified recombinant antibodies which may have negative impact on the structure and function of the antibodies. The disclosure also provides methods for reducing the percentage of such variant species without substantially compromising the yield of antibody production. More specifically, this disclosure describes methylglyoxal (MGO)-modified forms of Adalimumab in cell culture when Adalimumab is expressed in CHO cells using chemically defined media (CDM).

In one embodiment, modification of the side chain of certain arginines (e.g., R30 in CDR1 of Adalimumab) by MGO may result in the formation of a five-member ring originating at the guanidinium terminal of the side chain which may further penetrate into the TNF-alpha structure. These MGO modifications may impede Adalimumab's ability to bind TNF-alpha due to steric constraints.

In one embodiment, control of acidic species heterogeneity may be attained by purifying a protein of interest from a mixture comprising the protein with an anion exchange (AEX) adsorbent material and an aqueous salt solution under loading conditions that permit both the protein of interest and non-target proteins to bind to the AEX adsorbent, wherein the bound protein of interest is subsequently recovered with a wash buffer comprising the same aqueous salt solution used in the equilibration (i.e. loading) buffer. In one aspect, the aqueous salt solution used as both the loading and wash buffer has a pH that is greater than the isoelectric point (pI) of the protein of interest.

In another embodiment, the disclosed purification method may include adjusting the conductivity and/or pH of the aqueous salt solution. In one aspect, the adjustments may include decreasing the conductivity of the aqueous salt solution. In another aspect, the adjustment to achieve the desired control over acidic species heterogeneity may involve an increase in the load conductivity of the solution. In another aspect, the adjustment may increase the pH of the aqueous salt solution. In another aspect, the adjustment to achieve the desired control over acidic species heterogeneity may involve a decrease in the pH of the aqueous salt solution. Such increases and/or decreases in the conductivity and/or pH may be of a magnitude of 1%, 5%, 10%, 15%, 20%, 25%, 30%, 35%, 40%, 45%, 50%, 55%, 60%, 65%, 70%, 75%, 80%, 85%, 90%, 95%, or 100%, and ranges within one or more of the preceding, of the conductivity and/or pH of the aqueous salt solution.

In another embodiment, the conductivity and pH of the aqueous salt solution is adjusted by increasing or decreasing the concentration of a cationic agent and maintaining a constant concentration of an anionic agent in the aqueous salt solution. In one aspect, the anionic agent is maintained at a concentration of between about 0.05 mM and 100 mM, or between about 0.1 mM and 90 mM, or between about 0.5 mM and 80 mM, or between about 1 mM and 70 mM, or between about 1.5 mM and 60 mM, or between about 2 mM and 50 mM, or between about 2.5 mM and 40 mM, or between about 3 mM and 30 mM, or between about 3.5 mM and 25 mM, or between about 4 mM and 20 mM, or between about 4.5 mM and 15 mM, or between about 4.5 mM and 10 mM, or between about 5 mM and 7 mM. In another aspect, the anionic agent is maintained at a concentration of about 5 mM. In another aspect, the anionic agent is maintained at a concentration of about 10 mM. In another aspect, the anionic agent is maintained at a concentration of about 18.5 mM.

In another embodiment, the concentration of the cationic agent in the aqueous salt solution is increased or decreased to achieve a pH of between about 5 and 12, or between about 5.5 and 11.5, or between about 6 and 11, or between about 6.5 and 10.5, or between about 7 and 10, or between about 7.5 and 9.5, or between about 8 and 9, or between about 8.5 and 9. In certain embodiments, the concentration of cationic agent is increased or decreased in the aqueous salt solution to achieve a pH of 8.8. In certain embodiments, the concentration of cationic agent in the aqueous salt solution is increased or decreased to achieve a pH of 9.

In another embodiment, the protein load of the protein mixture is adjusted to a protein load of between about 50 g/L and 500 g/L, or between about 100 g/L and 450 g/L, or between about 120 g/L and 400 g/L, or between about 125 g/L and 350 g/L, or between about 130 g/L and 300 g/L or between about 135 g/L and 250 g/L, or between about 140 g/L and 200 g/L, or between about 145 g/L and 200 g/L, or between about 150 g/L and 200 g/L, or between about 155 g/L and 200 g/L, or between about 160 g/L and 200 g/L. In certain embodiments, the protein load of the protein or antibody mixture is adjusted to a protein load of about 100 g/L. In certain embodiments, the protein load of the protein or antibody mixture is adjusted to a protein load of about 20 g/L. In certain embodiments, the protein load of the protein or antibody mixture is adjusted to a protein load of about 105 g/L. In certain embodiments, the protein load of the protein or antibody mixture is adjusted to a protein load of about 140 g/L. In certain embodiments, the protein load of the protein or antibody mixture is adjusted to a protein load of about 260 g/L. In certain embodiments, the protein load of the protein or antibody mixture is adjusted to a protein load of about 300 g/L.

In another embodiment, the concentration of cationic agent in the aqueous salt solution is increased or decreased in an amount effective to reduce the amount of acidic species heterogeneity in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, or 100%, and ranges within one or more of the preceding, when the aqueous salt solution is used as a load and wash buffer to purify the protein of interest (for example, an antibody) from the sample containing the protein.

In another embodiment, the anionic agent is acetate, citrate, chloride anion, sulphate, phosphate or combinations thereof. In certain embodiments, the cationic agent is sodium, Tris, tromethalmine, ammonium cation, arginine, or combinations thereof.

By way of example but not limitation, as detailed in this disclosure, up to 60% of the acidic species in an antibody preparation was removed when the antibody was purified using chromatography comprising an anion exchange adsorbent material, a protein load of 150 g/L, and a load/wash buffer containing 5 mM Acetate/Arginine at pH 8.8.

In another embodiment of the instant disclosure, control of acidic species heterogeneity can be attained by purifying a protein of interest from a mixture comprising the protein with a cation exchange (CEX) adsorbent material and an aqueous salt solution under loading conditions that permit both the protein of interest and non-target proteins to bind to the CEX adsorbent, washing off the acidic species, charged variants, molecular variants and impurities using the same buffer conditions as the loading buffer, and eluting the bound protein target from the CEX adsorbent with a buffer having a higher conductivity than the loading buffer. In certain embodiments, the aqueous salt solution used as both the loading and wash buffer has a pH that is lower than the isoelectric point (pI) of the protein of interest.

In another embodiment, the purification method may include adjusting the conductivity and/or pH of the aqueous solution. In certain embodiments, such adjustments will be to decrease the conductivity, while in other embodiments the necessary adjustment to achieve the desired control over acidic species heterogeneity will involve an increase in the load conductivity. In certain embodiments, such adjustments will also be to increase the pH of the aqueous salt solution, while in other embodiments the necessary adjustment to achieve the desired control over acidic species heterogeneity will involve a decrease in the pH of the aqueous salt solution. Such increases and/or decreases in the conductivity and/or pH can be of a magnitude of 1%, 5%, 10%, 15%, 20%, 25%, 30%, 35%, 40%, 45%, 50%, 55%, 60%, 65%, 70%, 75%, 80%, 85%, 90%, 95%, or 100%, and ranges within one or more of the preceding, of the conductivity and/or pH of the aqueous salt solution.

In certain embodiments, the conductivity and pH of the aqueous salt solution is adjusted by increasing or decreasing the concentration of a anionic agent and maintaining a constant concentration of a cationic agent in the aqueous salt solution. In certain embodiments, the cationic agent is maintained at a concentration of between about 0.5 mM and 500 mM, or between about 1 mM and 450 mM, or between about 5 mM and 400 mM, or between about 10 mM and 350 mM, or between about 15 mM and 300 mM, or between about 20 mM and 250 mM, or between about 25 mM and 200 mM, or between about 30 mM and 150 mM, or between about 35 mM and 100 mM, or between about 40 mM and 50 mM. In certain embodiments, the anionic agent is maintained at a concentration of about 15 mM, or about 20 mM, or about 25 mM, or about 30 mM, or about 35 mM, or about 40 mM, or about 45 mM, or about 50 mM, or about 60 mM, or about 65 mM, or about 75 mM, or about 90 mM, or about 115 mM, or about 120 mM, or about 125 mM, or about 135 mM, or about 140 mM, or about 145 mM, or about 150 mM, or about 175 mM, or about 250 mM, or about 275 mM, or about 300 mM, or about 350 mM, or about 375 mM, or about 400 mM.

In certain embodiments, the concentration of the anionic agent in aqueous salt solution is increased or decreased to achieve a pH of between about 2 and 12, or between about 2.5 and 11.5, or between about 3 and 11, or between about 3.5 and 10.5, or between about 4 and 10, or between about 4.5 and 9.5, or between about 5 and 9, or between about 5.5 and 8.5, or between about 6 and 8, or between about 6.5 and 7.5. In certain embodiments, the concentration of anionic agent is increased or decreased in the aqueous salt solution to achieve a pH of 5, or 5.5, or 6, or 6.5, or 6.8, or 7.5.

In certain embodiments, the protein load of the protein mixture is adjusted to a protein load of between about 50 and 500 g/L, or between about 100 and 450 g/L, or between about 120 and 400 g/L, or between about 125 and 350 g/L, or between about 130 and 300 g/L or between about 135 and 250 g/L, or between about 140 and 200 g/L, or between about 145 and 150 g/L. In certain embodiments, the protein load of the protein or antibody mixture is adjusted to a protein load of about 40 g/L.

In certain embodiments, the concentration of anionic agent in the aqueous salt solution is increased or decreased in an amount effective to reduce the amount of acidic species heterogeneity in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, or 100%, and ranges within one or more of the preceding, when the aqueous salt solution is used as a load and wash buffer to purify the protein of interest (for example, an antibody) from the sample containing the protein.

In certain embodiments, the cationic agent is sodium, Tris, tromethalmine, ammonium cation, arginine, or combinations thereof. In certain embodiments, the anionic agent is acetate, citrate, chloride anion, sulphate, phosphate or combinations thereof.

By way of example but not limitation, as detailed in this disclosure, the presence of acidic species in an antibody preparation was reduced by 6.5% from starting material after purification using a cation exchange adsorbent material, and a load and wash buffer comprising 140 mM Tris at pH 7.5.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the disclosure may be more readily understood, select terms are defined below.

The term "antibody" refers to an immunoglobulin (Ig) molecule, which is generally comprised of four polypeptide chains, two heavy (H) chains and two light (L) chains, or a functional fragment, mutant, variant, or derivative thereof, that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The heavy chain variable region (domain) is also designated as VDH in this disclosure. The CH is comprised of three domains, CH1, CH2 and CH3. Each light chain is comprised of a light chain variable region (VL) and a light chain constant region (CL). The CL is comprised of a single CL domain. The light chain variable region (domain) is also designated as VDL in this disclosure. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "antigen-binding portion" of an antibody (or "antibody portion"), as used herein, refers to one or more fragments of an antibody that retain the ability to specifically bind to an antigen (e.g., hTNF-alpha). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH I domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "biological activity" refers to any one or more biological properties of a molecule (whether present naturally as found in vivo, or provided or enabled by recombinant means). Biological properties include, but are not limited to, binding a receptor or receptor ligand, inducing cell proliferation, inhibiting cell growth, inducing other cytokines, inducing apoptosis, and enzymatic activity.

The term "neutralizing" refers to counteracting the biological activity of an antigen/ligand when a binding protein specifically binds to the antigen/ligand. In an embodiment, the neutralizing binding protein binds to an antigen/ligand (e.g., a cytokine) and reduces its biologically activity by at least about 20%, 40%, 60%, 80%, 85% or more.

"Specificity" refers to the ability of a binding protein to selectively bind an antigen/ligand.

"Affinity" is the strength of the interaction between a binding protein and an antigen/ligand, and is determined by the sequence of the binding domain(s) of the binding protein as well as by the nature of the antigen/ligand, such as its size, shape, and/or charge. Binding proteins may be selected for affinities that provide desired therapeutic end-points while minimizing negative side-effects. Affinity may be measured using methods known to one skilled in the art (US 20090311253).

The term "potency" refers to the ability of a binding protein to achieve a desired effect, and is a measurement of its therapeutic efficacy. Potency may be assessed using methods known to one skilled in the art (US 20090311253).

The term "cross-reactivity" refers to the ability of a binding protein to bind a target other than that against which it was raised. Generally, a binding protein will bind its target tissue(s)/antigen(s) with an appropriately high affinity, but will display an appropriately low affinity for non-target normal tissues. Individual binding proteins are generally selected to meet two criteria. (1) Tissue staining appropriate for the known expression of the antibody target. (2) Similar staining pattern between human and tox species (mouse and cynomolgus monkey) tissues from the same organ. These and other methods of assessing cross-reactivity are known to one skilled in the art (US 20090311253).

The term "biological function" refers the specific in vitro or in vivo actions of a binding protein. Binding proteins may target several classes of antigens/ligands and achieve desired therapeutic outcomes through multiple mechanisms of action. Binding proteins may target soluble proteins, cell surface antigens, as well as extracellular protein deposits. Binding proteins may agonize, antagonize, or neutralize the activity of their targets. Binding proteins may assist in the clearance of the targets to which they bind, or may result in cytotoxicity when bound to cells. Portions of two or more antibodies may be incorporated into a multivalent format to achieve distinct functions in a single binding protein molecule. The in vitro assays and in vivo models used to assess biological function are known to one skilled in the art (US 20090311253).

The term "solubility" refers to the ability of a protein to remain dispersed within an aqueous solution. The solubility of a protein in an aqueous formulation depends upon the proper distribution of hydrophobic and hydrophilic amino acid residues, and therefore, solubility can correlate with the production of correctly folded proteins. A person skilled in the art will be able to detect an increase or decrease in solubility of a binding protein using routine HPLC techniques and methods known to one skilled in the art (US 20090311253).

Binding proteins may be produced using a variety of host cells or may be produced in vitro, and the relative yield per effort determines the "production efficiency." Factors influencing production efficiency include, but are not limited to, host cell type (prokaryotic or eukaryotic), choice of expression vector, choice of nucleotide sequence, and methods employed. The materials and methods used in binding protein production, as well as the measurement of production efficiency, are known to one skilled in the art (US 20090311253).

The term "conjugate" refers to a binding protein, such as an antibody, that is chemically linked to a second chemical moiety, such as a therapeutic or cytotoxic agent. The term "agent" includes a chemical compound, a mixture of chemical compounds, a biological macromolecule, or an extract made from biological materials. In an embodiment, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

The term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Other vectors include RNA vectors. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, other forms of expression vectors are also included, such as viral vectors (e.g., replication defective retroviruses, adenoviruses and adeno-associated viruses), which serve equivalent functions. A group of pHybE vectors (U.S. Patent Application Ser. No. 61/021,282) were used for parental binding protein cloning.

The terms "recombinant host cell" or "host cell" refer to a cell into which exogenous DNA has been introduced. Such terms refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells. In an embodiment, eukaryotic cells include protist, fungal, plant and animal cells. In another embodiment, host cells include but are not limited to the prokaryotic cell line E. Coli; mammalian cell lines CHO, HEK293, COS, NS0, SP2 and PER.C6; the insect cell line Sf9; and the fungal cell Saccharomyces cerevisiae.

The term "transfection" encompasses a variety of techniques commonly used for the introduction of exogenous nucleic acid (e.g., DNA) into a host cell, e.g., electroporation, calcium-phosphate precipitation, DEAE-dextran transfection and the like.

The term "cytokine" refers to a protein released by one cell population that acts on another cell population as an intercellular mediator. The term "cytokine" includes proteins from natural sources or from recombinant cell culture and biologically active equivalents of the native sequence cytokines.

The term "biological sample" means a quantity of a substance from a living thing or formerly living thing. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

The term "component" refers to an element of a composition. In relation to a diagnostic kit, for example, a component may be a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample. Thus, a "component" can include a polypeptide or other analyte as above, that is immobilized on a solid support, such as by binding to an anti-analyte (e.g., anti-polypeptide) antibody. Some components can be in solution or lyophilized for reconstitution for use in an assay.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

The term "Fc region" defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. Replacements of amino acid residues in the Fc portion to alter antibody effector function are known in the art (e.g., U.S. Pat. Nos. 5,648,260 and 5,624,821). The Fc region mediates several important effector functions, e.g., cytokine induction, antibody dependent cell mediated cytotoxicity (ADCC), phagocytosis, complement dependent cytotoxicity (CDC), and half-life/clearance rate of antibody and antigen-antibody complexes. In some cases these effector functions are desirable for a therapeutic immunoglobulin but in other cases might be unnecessary or even deleterious, depending on the therapeutic objectives.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "CDR" means a complementarity determining region within an immunoglobulin variable region sequence. There are three CDRs in each of the variable regions of the heavy chain and the light chain, which are designated CDR1, CDR2 and CDR3, for each of the heavy and light chain variable regions. The term "CDR set" refers to a group of three CDRs that occur in a single variable region capable of binding the antigen. The exact boundaries of these CDRs have been defined differently according to different systems. The system described by Kabat (Kabat et al. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk (1987) J. Mol. Biol. 196:901-917; Chothia et al. (1989) Nature 342:877-883) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The term "epitope" means a region of an antigen that is bound by a binding protein, e.g., a polypeptide and/or other determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In an embodiment, an epitope comprises the amino acid residues of a region of an antigen (or fragment thereof) known to bind to the complementary site on the specific binding partner. An antigenic fragment can contain more than one epitope. In certain embodiments, a binding protein specifically binds an antigen when it recognizes its target antigen in a complex mixture of proteins and/or macromolecules. Binding proteins "bind to the same epitope" if the antibodies cross-compete (one prevents the binding or modulating effect of the other). In addition, structural definitions of epitopes (overlapping, similar, identical) are informative; and functional definitions encompass structural (binding) and functional (modulation, competition) parameters. Different regions of proteins may perform different functions. For example specific regions of a cytokine interact with its cytokine receptor to bring about receptor activation whereas other regions of the protein may be required for stabilizing the cytokine. To abrogate the negative effects of cytokine signaling, the cytokine may be targeted with a binding protein that binds specifically to the receptor interacting region(s), thereby preventing the binding of its receptor. Alternatively, a binding protein may target the regions responsible for cytokine stabilization, thereby designating the protein for degradation. The methods of visualizing and modeling epitope recognition are known to one skilled in the art (US 20090311253).

"Pharmacokinetics" refers to the process by which a drug is absorbed, distributed, metabolized, and excreted by an organism. To generate a multivalent binding protein molecule with a desired pharmacokinetic profile, parent binding proteins with similarly desired pharmacokinetic profiles are selected. The PK profiles of the selected parental binding proteins can be easily determined in rodents using methods known to one skilled in the art (US 20090311253).

"Bioavailability" refers to the amount of active drug that reaches its target following administration. Bioavailability is function of several of the previously described properties, including stability, solubility, immunogenicity and pharmacokinetics, and can be assessed using methods known to one skilled in the art (US 20090311253).

The term "$K_{on}$" means the on rate constant for association of a binding protein (e.g., an antibody) to the antigen to form the, antibody/antigen complex. The term "$K_{on}$" also means "association rate constant", or "ka", as is used interchangeably herein. This value indicating the binding rate of a binding protein to its target antigen or the rate of complex formation between a binding protein, e.g., an antibody, and antigen also is shown by the equation below:

The term "$K_{off}$" means the off rate constant for dissociation, or "dissociation rate constant", of a binding protein (e.g., an antibody) from the, antibody/antigen complex as is known in the art. This value indicates the dissociation rate of a binding protein, e.g., an antibody, from its target antigen or separation of Ab–Ag complex over time into free antibody and antigen as shown by the equation below:

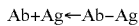

The terms "$K_d$" and "equilibrium dissociation constant" means the value obtained in a titration measurement at equilibrium, or by dividing the dissociation rate constant ($K_{off}$) by the association rate constant ($K_{on}$). The association rate constant, the dissociation rate constant and the equilibrium dissociation constant, are used to represent the binding affinity of a binding protein (e.g., an antibody) to an antigen. Methods for determining association and dissociation rate constants are well known in the art. Using fluorescence based techniques offers high sensitivity and the ability to examine samples in physiological buffers at equilibrium. Other experimental approaches and instruments such as a BIAcore® (biomolecular interaction analysis) assay, can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.), can also be used.

The term "variant" means a polypeptide that differs from a given polypeptide in amino acid sequence or in post-translational modification. The difference in amino acid sequence may be caused by the addition (e.g., insertion), deletion, or conservative substitution of amino acids, but that retains the biological activity of the given polypeptide (e.g., a variant TNF-alpha antibody can compete with anti-TNF-alpha antibody for binding to TNF-alpha). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes in a protein can be substituted and the protein still retains protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. The term "variant" also includes polypeptide or fragment thereof that has been differentially processed, such as by proteolysis, phosphorylation, or other post-translational modification, yet retains its biological activity or antigen reactivity, e.g., the ability to bind to TNF-alpha. The term "variant" encompasses fragments of a variant unless otherwise defined. A variant may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to the wild-type sequence.

The difference in post-translational modification may be effected by addition of one or more chemical groups to the amino acids of the modified molecule, or removal of one or more such groups from the molecule. Examples of modification may include but are not limited to, phosphorylation, glysosylation, or MGO modification.

It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Identification of Different Forms of MGO-mAb

In a traditional process for making Adalimumab, antibody expression typically takes place by using Hydrolysate and Phytone as raw materials. When adalimumab was expressed with CHO cells using chemically defined media (CDM), the percentage of acidic species as defined by the weak cation exchange chromatography method increased as compared to the percentage of acidic species generated by the traditional production process. Specifically, two distinct early eluting chromatographic peaks were observed as shown in FIG. 1. The peaks labeled as Lys 0, Lys 1 and Lys 2 are antibody without C-terminal Lys, with one C-terminal Lys and with two C-terminal Lys on the heavy chains, respectively. The top trace is from adalimumab produced using chemically defined media (CDM) and the bottom trace is from adalimumab produced using yeastolate. Two peaks were observed in antibody expressed in cell culture using CDM and are denoted by Fractions 1 and 2, respectively. These peaks are unique to adalimumab production with CDM. The peaks were subsequently isolated using weak cation exchange fractionation.

Figure 2:
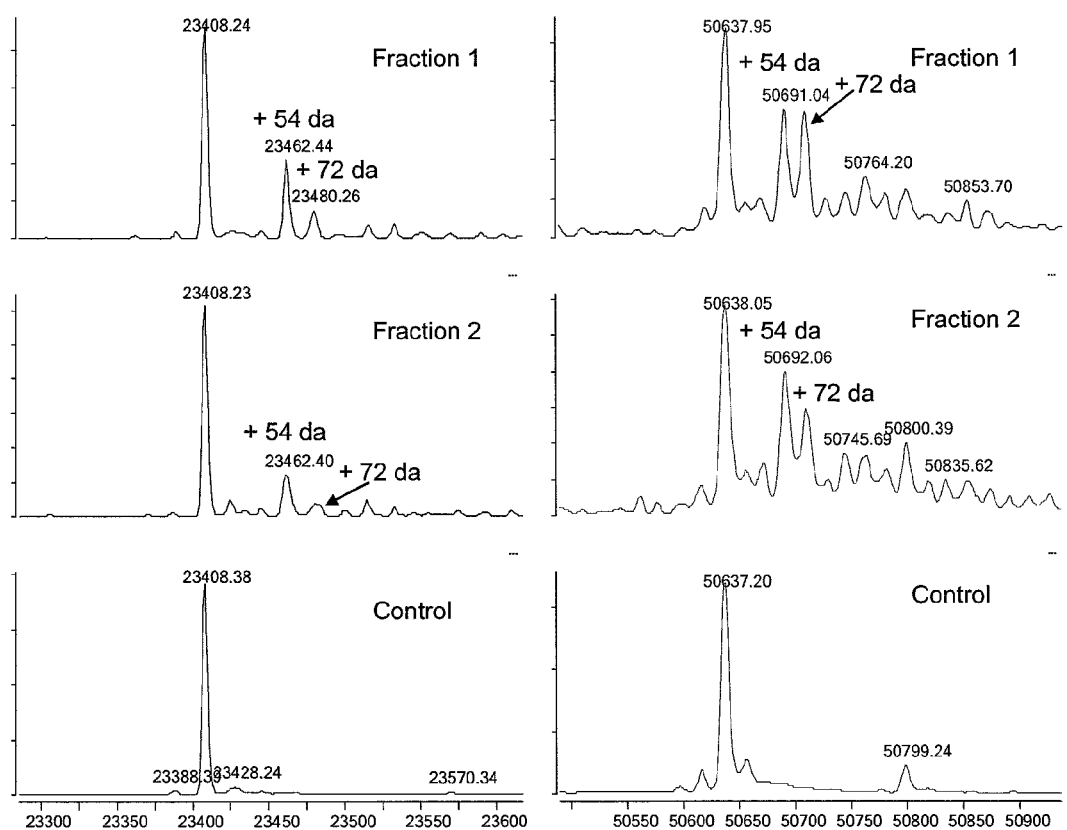
FIG. 2 shows deconvoluted mass spectra of the light chain and heavy chains in fractions 1 and 2.

Analysis of the isolated peaks by reduced LC/MS revealed mass spectra of the expected values for the adalimumab heavy chain and light chain but with additional peak corresponding to mass increases of +54 Da and +72 Da with additional lower intensity peaks which are likely due to additional modifications at multiple sites of the respective chains (FIG. 2). As shown in FIG. 2 left panel, three major peaks corresponding to the theoretical molecular weight of the light chain at 23408 Da plus masses of 23462 and 23480 were observed. The two peaks that shift from the theoretical molecular weight diverge from the expected mass by increases of 54 and 72 daltons, respectively. As shown in FIG. 2 Right Panel, three peaks corresponding to the theoretical molecular weight of the heavy chain at 50637 Da plus an additional ladder of masses corresponding to 54 and 72 Da increases were observed. Peaks with these molecular weight increases were observed for both the light chain and heavy chain from fractions 1 and 2 but were noticeably absent from the Lys-0 controls (bottom spectra of FIG. 2).

Figure 3:
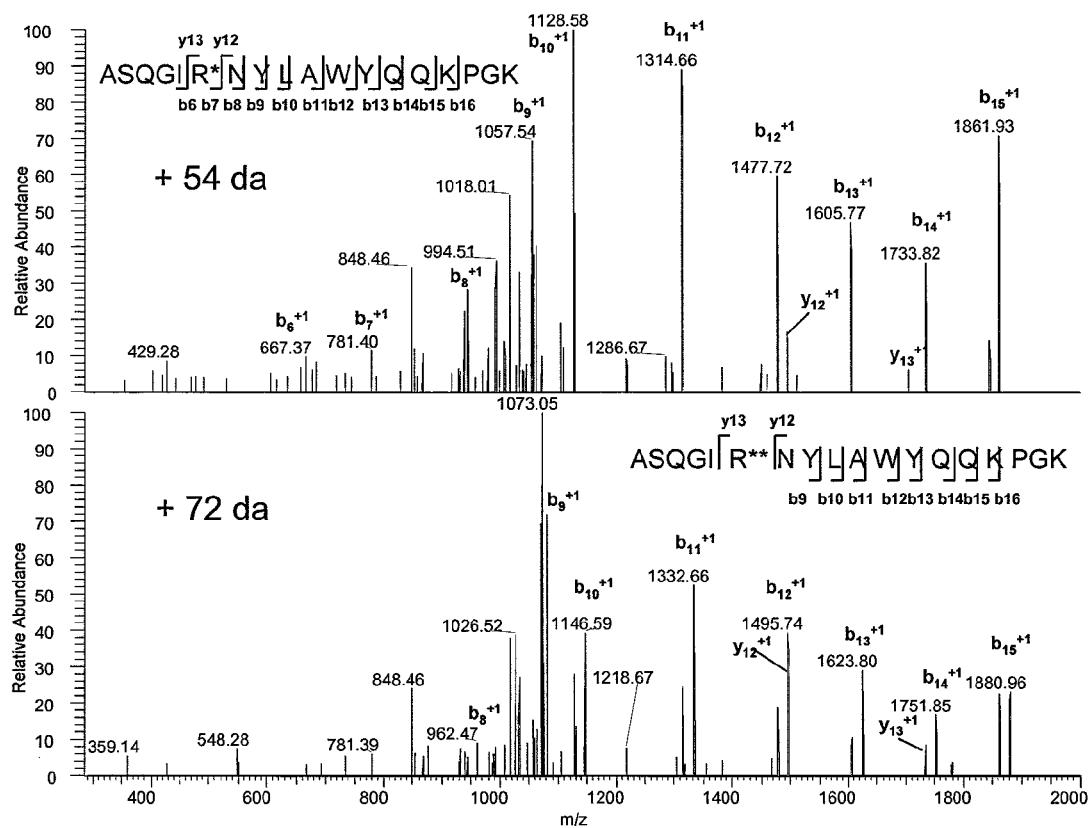
FIG. 3 shows representative MS/MS mass spectra of peptides containing Arg residues modified by MGO. Two peptides are shown: ASQGIR*NYLAWYQQKPGK (SEQ ID NO. 3) and ASQGIR**NYLAWYQQKPGK (SEQ ID NO. 4), wherein R* and R** are the MGO-modified Arginine 30 residue resulting in a molecular weight increase of 54 Da and 72 Da, respectively.

The peaks were subsequently analyzed by peptide mapping with LC/MS/MS detection. Modifications that resulted in the molecular weight increases of both 54 Da and 72 Da were localized to a particular Arg for this peptide and has resulted in a tryptic mis-cleavage (FIG. 3). This observation supports the hypothesis of hydroxylimidine conversion to a hydroimadazolone after loss of water. The results suggest that the modifications are localized to miscleaved tryptic peptides where the adduction is on the arginine side chain.

Figure 4:
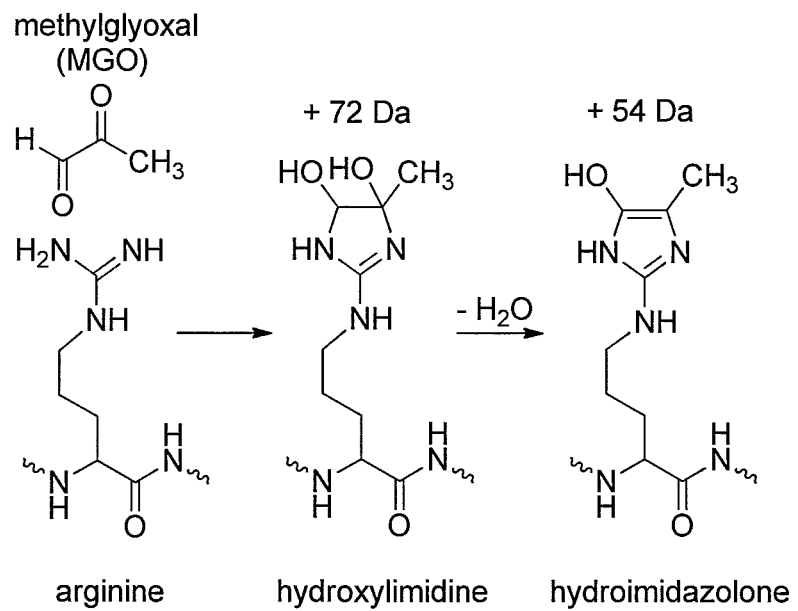
FIG. 4 shows chemical modification of arginine by MGO.

Based on these observations, it is likely that the adduction of the antibody was due to methylglyoxal (MGO) accumulation in cell cultures grown in the presence of chemically defined media (CDM). The reaction scheme for methylglyoxal modification of arginine residues is shown in FIG. 4. The initial adduction of MGO with an arginine side chain results in the formation of a hydroxylimidine with an observed mass increase of +72 Da. Following a dehydration to a hydroimadazolone, the resulting product has a +54 Da mass increase.

In order to confirm that an accumulation of methylglyoxal is the cause of the +54 Da and +72 Da mass increases associated with the early eluting acidic peaks, antibody was incubated with synthetic methylglyoxal and analyzed over a time course. WCX-10 fractionation was used to isolate zero lysine species, which is the adalimumab antibody with only the dominant main peak of the weak cation exchange chromatogram present. The 0 Lys species was incubated in the presence of 2.7 mM MGO over the course of five hours at 37 C.

Figure 5:
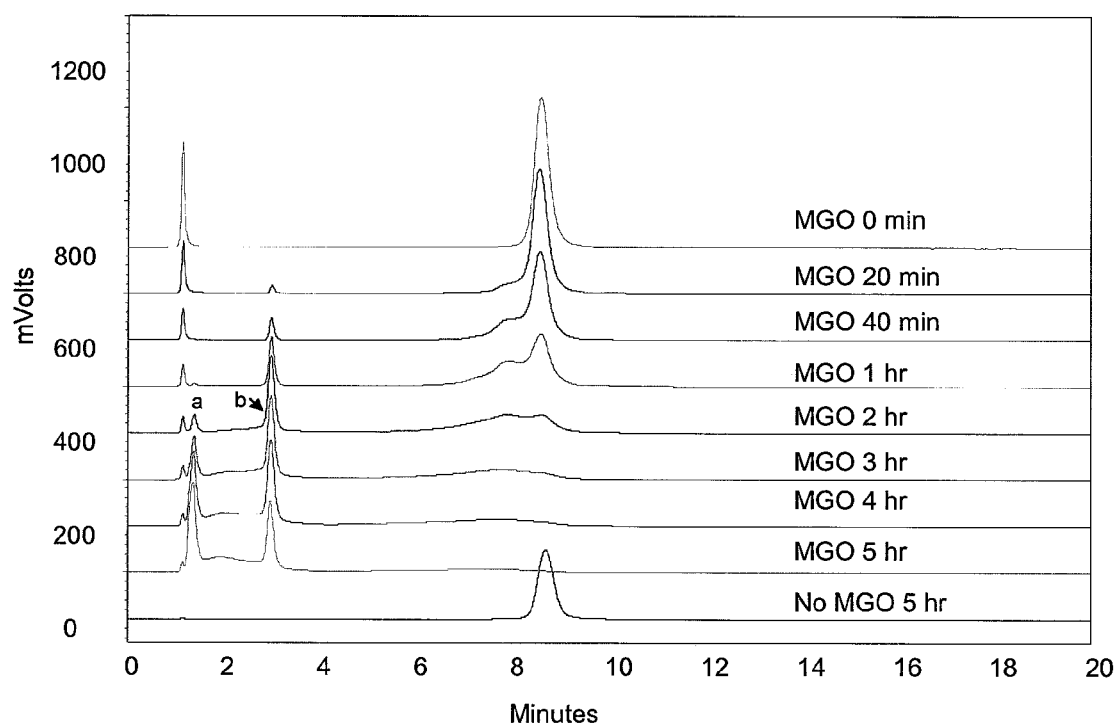
FIG. 5 shows modification of a purified 0 lysine fraction by MGO over a 5-hour time course.

As shown in FIG. 5, over the time course, nearly all of the 0 Lys was converted to the two distinct acidic peaks found in the initial material analyzed from the CDM expressions. The lysine 0 after incubation under the same condition without exposure to MGO is also shown as a control. Peaks a and b from the sample treated with MGO for 120 minutes were subsequently collected and analyzed by LC/MS to assess the level of chemical modifications which have resulted.

Figure 6:
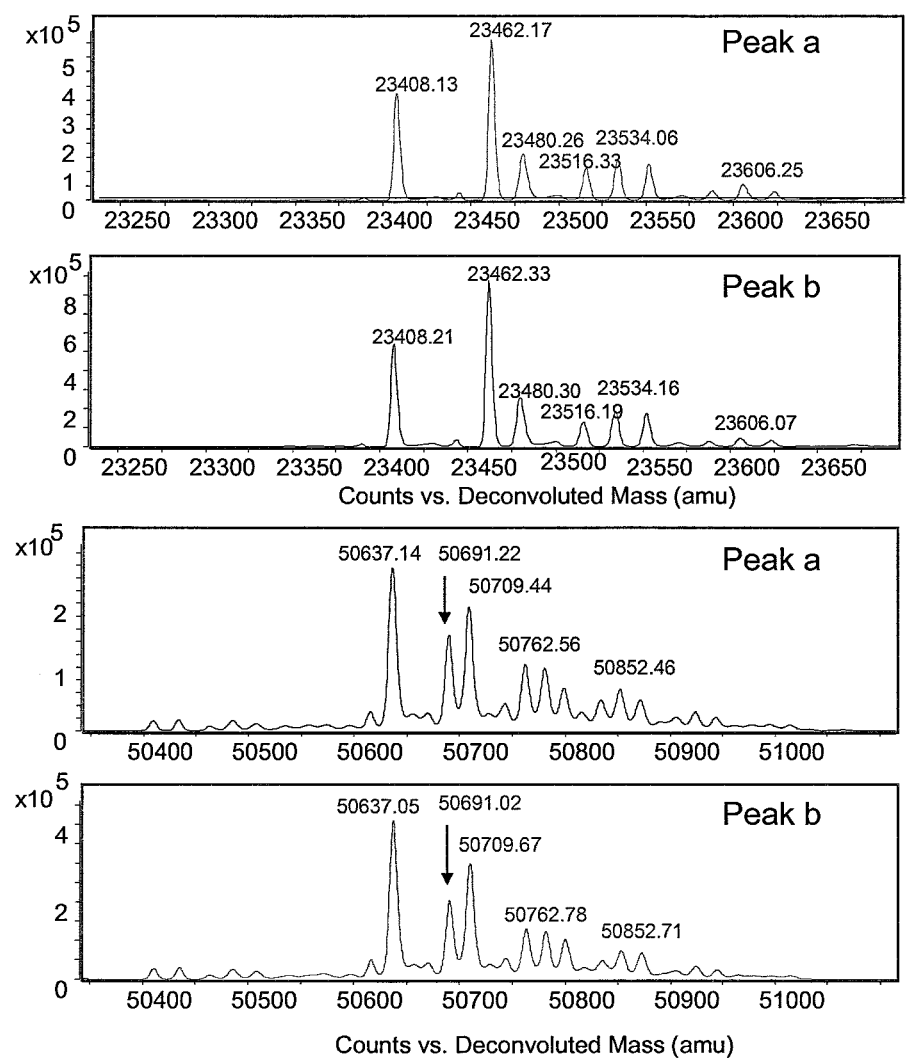
FIG. 6 shows the mass spectra of peaks a and b from FIG. 5.

Subsequent analysis of 0 Lys material incubated with MGO showed the previously observed ladder of +54 Da and +72 Da mass heterogeneity as a prevalent pattern in the mass spectra of both the adalimumab light chain and heavy chain (FIG. 6). More specifically, peaks a and b from the 0 Lys recombinant antibody species treated with MGO were fractionated and analyzed by reduced LC/MS. The top pane shows the corresponding light chain mass spectra of the two peaks and the bottom pane depicts the heavy chain for the fractionated peaks. Mass heterogeneity of the chains corresponding to +54 Da and +72 Da were observed for both fractions. The resulting modifications are in agreement with the observations found in the cell culture acidic peaks supporting the previous data that the modification is due to methylglyoxal. Thus, fractionation of the acidic-shifted 0 Lys material followed by LC/MS/MS tryptic mapping confirmed that MGO modification of arginine residues was the cause of the observed adductions.

Figure 7:
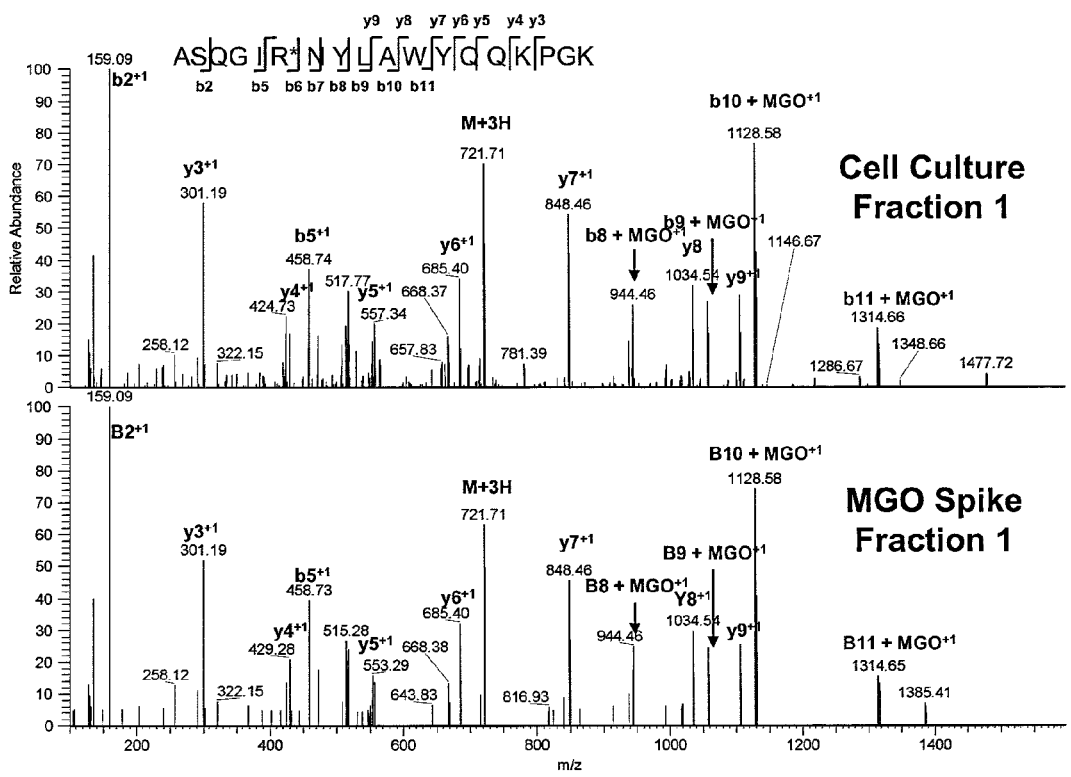
FIG. 7 shows comparison of peptide (SEQ ID NO. 3) MS/MS data between acidic fraction 1 from cell culture and acidic fraction 1 from methylglyoxal incubation.

In addition, acid species from both cell culture and the MGO spike were compared to each other by LC/MS/MS. The resulting MS/MS spectra showed fragmentation profiles that were highly comparable for mis-cleavages at arginine residues with the MGO adduction characteristic +54 Da and +72 Da mass increases (FIG. 7). The data provide a confirmation that the acidic peaks resulting from the use of chemically defined media are due to modifications of the expressed adalimumab recombinant antibody by methylglyoxal which has accumulated in the cell culture bioreactor. Moreover, the modification of the arginine may influence the fragmentation of the peptide backbone. The strong similarities between the two mass spectra further support the notion that the arginine has undergone a modification which may result in destabilization of the peptide backbone.

Example 2

Functional Liabilities Associated with Methylglyoxal Modifications to Adalimumab Antibodies Methylglyoxal modifications of arginine residues lead to miscleavages due to the steric constraints imparted by the adducted MGO to the active site of trypsin. In order to better quantitate and determine all susceptible arginine residues in the adalimumab primary structure, an endoprotease Lys-C digestion was performed where arginine residues were no longer recognized as target substrates in the peptide mapping protocol. All Lys-C peptides were evaluated using the Sequest algorithm against the FASTA sequence for adalimumab. Several sites were identified as potential susceptible sites but one site of particular susceptibility was identified at R30 of the light chain. The sequences of the light chain and heavy chain of the Adalimumab D2E7 are designated as SEQ ID No. 1 and SEQ ID No. 2, respectively. A list of all potential susceptible arginine residues is shown in Table 1. Different sites may have different level of susceptibility to MGO modification. Not all sites have to be modified by MGO in a single molecule. Table 2 lists peptide fragments on Adalimumab that are susceptible to modification by methylglyoxal.

TABLE 1

Potential Sites of MGO modification in Adalimumab

| Ab Chain Type | Adalimumab Light Chain (SEQ ID No. 1) | Adalimumab Heavy Chain (SEQ ID No. 2) |
| --- | --- | --- |
| Arginine Sites | Arginine 30<br>Arginine 93<br>Arginine 108 | Arginine 16<br>Arginine 259<br>Arginine 359<br>Arginine 420 |

TABLE 2

List of peptides susceptible to modification by methylglyoxal

| Sequence (SEQ ID NO) | Activation Type | Modifications | Charge | m/z [Da] | MH+ [Da] | RT [min] | MS Order |
| --- | --- | --- | --- | --- | --- | --- | --- |
| EPQVYTLPPSrDELTK(5) | HCD | R11(MGO(R)72) | 2 | 972.9988 | 1944.99 | 27.71 | MS2 |
| EPQVYTLPPSrDELTK(5) | CID | R11(MGO(R)72) | 3 | 649.0014 | 1944.99 | 27.72 | MS2 |
| EPQVYTLPPSrDELTK(5) | CID | R11(MGO) | 3 | 642.9988 | 1926.982 | 27.81 | MS2 |

TABLE 2-continued

List of peptides susceptible to modification by methylglyoxal

| Sequence (SEQ ID NO) | Activation Type | Modifications | Charge | m/z [Da] | MH+ [Da] | RT [min] | MS Order |
|---|---|---|---|---|---|---|---|
| EPQVYTLPPSrDELTK(5) | HCD | R11(MGO) | 3 | 642.9988 | 1926.982 | 27.82 | MS2 |
| EPQVYTLPPSrDELTK(5) | CID | R11(MGO) | 2 | 963.9942 | 1926.981 | 27.88 | MS2 |
| EPQVYTLPPSrDELTK(5) | HCD | R11(MGO) | 2 | 963.9942 | 1926.981 | 27.89 | MS2 |
| EVQLVESGGGLVQPGrSLR(6) | CID | R16(MGO(R)72) | 2 | 1027.055 | 2053.103 | 32 | MS2 |
| EVQLVESGGGLVQPGrSLR(6) | HCD | R16(MGO(R)72) | 2 | 1027.055 | 2053.103 | 32.01 | MS2 |
| EVQLVESGGGLVQPGrSLR(6) | CID | R16(MGO) | 3 | 679.0353 | 2035.091 | 32.11 | MS2 |
| EVQLVESGGGLVQPGrSLR(6) | CID | R16(MGO) | 2 | 1018.05 | 2035.092 | 32.13 | MS2 |
| EVQLVESGGGLVQPGrSLR(6) | HCD | R16(MGO) | 2 | 1018.05 | 2035.092 | 32.15 | MS2 |
| DIQMTQSPSSLSASVGDNTITcR(7) | HCD | R18(MGO), C23(Carboxymethyl) | 3 | 888.7587 | 2664.261 | 35.6 | MS2 |
| DIQMTQSPSSLSASVGDNTITcR(7) | HCD | R18(MGO), C23(Carboxymethyl) | 3 | 888.7583 | 2664.26 | 36.63 | MS2 |
| YNrAPYTFGQGTK(8) | CID | R3(MGO(R)72) | 2 | 787.8835 | 1574.76 | 17.61 | MS2 |
| YNrAPYTFGQGTK(8) | HCD | R3(MGO(R)72) | 2 | 787.8835 | 1574.76 | 17.62 | MS2 |
| YNrAPYTFGQGTK(8) | CID | R3(MGO(R)72) | 3 | 525.5911 | 1574.759 | 17.63 | MS2 |
| YNrAPYTFGQGTK(8) | HCD | R3(MGO(R)72) | 3 | 525.5911 | 1574.759 | 17.64 | MS2 |
| YNrAPYTFGQGTKVEIK(9) | CID | R3(MGO(R)72) | 2 | 1022.461 | 2043.916 | 46.16 | MS2 |
| SLrLScAASGFTFDDYAMHVVVR(10) | CID | R3(MGO(R)72), C6(Carboxymethyl) | 3 | 888.4062 | 2663.204 | 49.36 | MS2 |
| SLrLScAASGFTFDDYAMHVVVR(10) | HCD | R3(MGO(R)72), C6(Carboxymethyl) | 3 | 888.4062 | 2663.204 | 49.38 | MS2 |
| YNrAPYTFGQGTK(11) | CID | R3(MGO) | 2 | 778.8782 | 1556.749 | 17.49 | MS2 |
| YNrAPYTFGQGTK(11) | HCD | R3(MGO) | 2 | 778.8782 | 1556.749 | 17.5 | MS2 |
| YNrAPYTFGQGTK(11) | CID | R3(MGO) | 3 | 519.5878 | 1556.749 | 17.56 | MS2 |
| YNrAPYTFGQGTK(11) | HCD | R3(MGO) | 3 | 519.5878 | 1556.749 | 17.57 | MS2 |
| SFNrGEc(12) | HCD | R4(MGO), C7(Carboxymethyl) | 2 | 462.8614 | 924.7156 | 5.29 | MS2 |
| ASQGMLAWYQQKPGK(13) | CID | R6(MGO(R)72) | 3 | 727.3791 | 2180.123 | 32.15 | MS2 |
| ASQGMLAWYQQKPGK(13) | HCD | R6(MGO(R)72) | 3 | 727.3791 | 2180.123 | 32.16 | MS2 |
| ASQGIrNYLAWYQQKPGK(14) | CID | R6(MGO(R)72) | 2 | 1090.566 | 2180.125 | 32.2 | MS2 |
| ASQGIrNYLAWYQQKPGK(14) | HCD | R6(MGO(R)72) | 2 | 1090.566 | 2180.125 | 32.21 | MS2 |
| ASQGIrNYLAWYQQKPGK(14) | CID | R6(MGO) | 3 | 721.3756 | 2162.112 | 31.52 | MS2 |
| ASQGIrNYLAWYQQKPGK(14) | HCD | R6(MGO) | 3 | 721.3756 | 2162.112 | 31.53 | MS2 |
| ASQGIrNYLAWYQQKPGK(14) | CID | R6(MGO) | 2 | 1081.561 | 2162.115 | 31.55 | MS2 |
| ASQGIrNYLAWYQQKPGK(14) | HCD | R6(MGO) | 2 | 1081.561 | 2162.115 | 31.56 | MS2 |
| DTLMISrTPEVTcVVVDVSHEDPEVK(15) | CID | R7(MGO(R)72), C13(Carboxymethyl) | 3 | 1010.155 | 3028.451 | 44.42 | MS2 |
| DTLMISrTPEVTcVVVDVSHEDPEVK(15) | HCD | R7(MGO(R)72), C13(Carboxymethyl) | 3 | 1010.155 | 3028.451 | 44.43 | MS2 |
| DTLMISrTPEVTcVVVDVSHEDPEVK(15) | CID | R7(MGO), C13(Carboxymethyl) | 3 | 1004.152 | 3010.442 | 44.14 | MS2 |

TABLE 2-continued

List of peptides susceptible to modification by methylglyoxal

| Sequence (SEQ ID NO) | Activation Type | Modifications | Charge | m/z [Da] | MH+ [Da] | RT [min] | MS Order |
|---|---|---|---|---|---|---|---|
| DTLMISrTPEVTcVVVDVSHEDPEVK(15) | HCD | R7(MGO), C13(Carboxymethyl) | 3 | 1004.152 | 3010.442 | 44.15 | MS2 |

Figure 8:
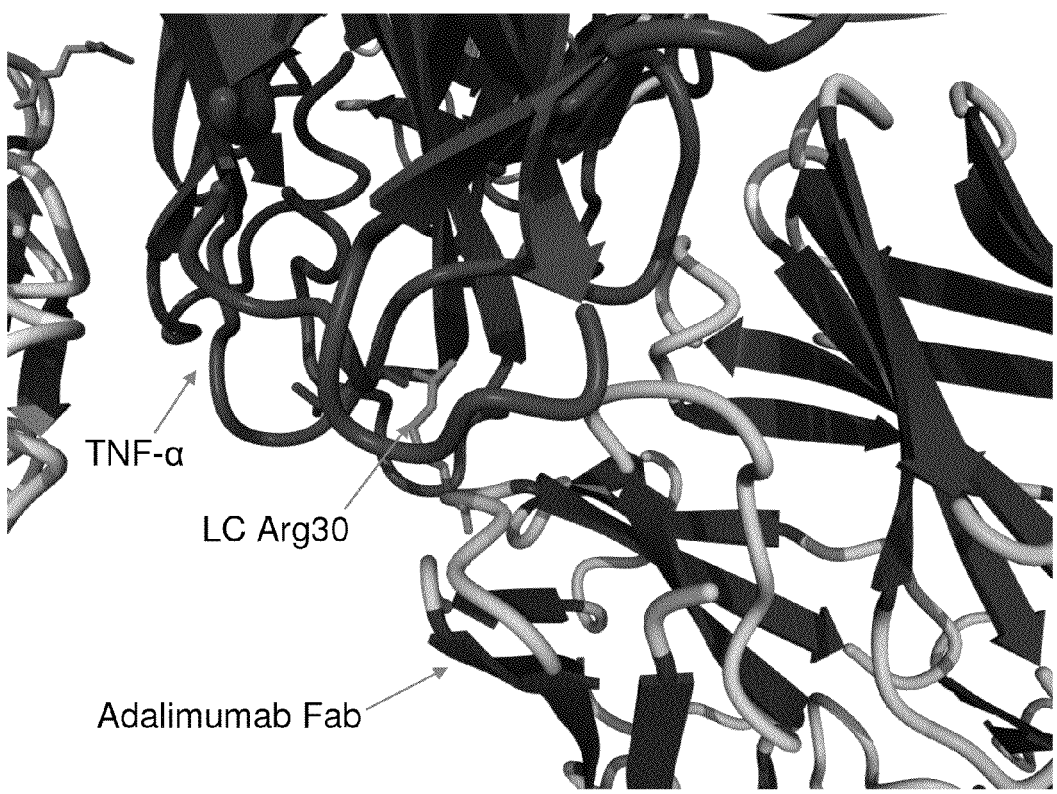
FIG. 8 shows the crystal structure of the adalimumab Fab subunit in complex with TNF-alpha, indicating that modification by MGO may cause conformational change which may impede adalimumab's ability to bind TNF-alpha.
Figure 10:
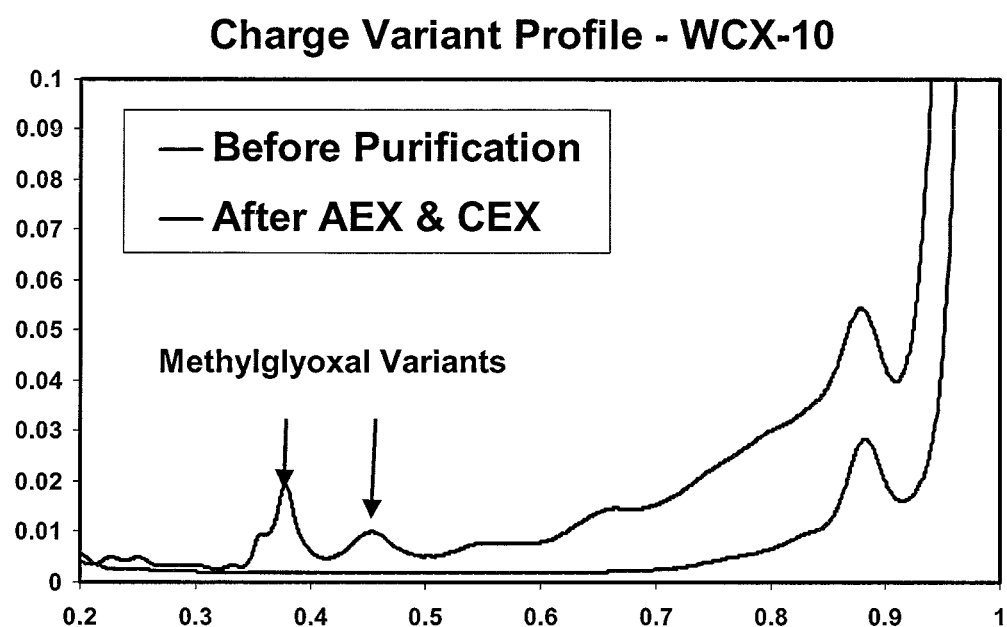
FIG. 10 shows comparison of acidic region affected by methylglyoxal before and after two-step chromatographic separation, wherein the top trace is an expanded view of the acidic region in which the two distinctive MGO peaks are denoted, and the lower trace shows a complete clearance of this acidic region and the MGO variants.

The crystal structure of the adalimumab Fab unit in complex with its cognate binding partner TNF-alpha shows that R30 is intimately involved in the contact surface between CDR1 and the antigen surface (FIG. 8). The figure shows the side chain of arginine 30 (indicated by arrow) protruding into the TNF-alpha structure (indicated by arrow). A modification of this side chain by MGO would result in the formation of a five-member ring originating at the guanidinium terminal of the side chain and further penetrating into the TNF-alpha structure. The MGO modification is therefore likely to impede adalimumab's ability to bind TNF-alpha due to steric constraints.

In order to further elucidate any functional liabilities associated with adalimumab and chemical modifications due to an accumulation of MGO in a cell culture expression using chemically defined media, an enriched MGO-modified fraction was isolated using weak cation exchange chromatography. A control fraction of a pure 0 Lys fraction was also obtained. The two fraction were analyzed by surface plasmon resonance to calculate the association and dissociation rates of TNF-alpha to the immobilized antibody. A three-fold reduction was observed for the MGO modified adalimumab as compared to the 0 Lys control (FIG. 9). Thus, it appears that the methylglyoxal modification of Arginine 30 (R30) of the light chain does impart a functional liability to the affected population of adalimumab drug substance. These data support the hypothesis that a chemical modification on the side chain of Arginine 30 of the light chain induces steric interference with the CDR1 and the TNF-alpha binding surface which may lead to a significant drop in adalimumab potency. It is therefore desirable to reduce the amount of this modified form of antibody in adalimumab drug substance or drug product.

Example 3

Removal of Methylglyoxal-Modified Adalimumab Using an AEX and/or CEX Strategy A chromatographic strategy was employed to remove the early eluting acidic region on the WCX-10 chromatogram. After the removal process is performed, adalimumab drug substance devoid of this region was generated. As disclosed herein, expression of adalimumab in chemically defined media may cause an increase of species eluting in this acidic region as a result of the accumulating MGO adducting to the positively charged guanidinium groups of the affected arginine residues. The disclosed chromatographic strategy helps clear this functional liability of the adalimumab preparation. The resulting adalimumab BDS is free of or substantially free of the negative impact from the methylglyoxal modification and has normal binding to its target, TNF-alpha.

The decision whether to use cationic exchange chromatography (CEX), anionic exchange chromatography (AEX), or both, to purify a protein is primarily based on the overall charge of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial protein mixture can be contacted with the ion exchange material by using any of a variety of techniques, e.g., using a batch purification technique or a chromatographic technique.

For example, ion exchange chromatography is used as a purification technique to separate the MGO-modified forms from the non-MGO-modified forms. Ion exchange chromatography separates molecules based on differences between the overall charge of the molecules. In the case of an antibody, the antibody has a charge opposite to that of the functional group attached to the ion exchange material, e.g., resin, in order to bind. For example, antibodies, which generally have an overall positive charge in a buffer having a pH below its pI, will bind well to cation exchange material, which contain negatively charged functional groups.

In ion exchange chromatography, charged patches on the surface of the solute are attracted by opposite charges attached to a chromatography matrix, provided the ionic strength of the surrounding buffer is low. Elution is generally achieved by increasing the ionic strength (i.e., conductivity) of the buffer to compete with the solute for the charged sites of the ion exchange matrix. Changing the pH and thereby altering the charge of the solute is another way to achieve elution of the solute. The change in conductivity and/or pH may be gradual (gradient elution) or stepwise.

Example 3.1

Removal of Methylglyoxal-Modified Adalimumab Using AEX

A process is described here for purifying a target protein product from both process and product related impurities. Specifically, a method is provided for reducing product related charge variants (i.e. acidic and basic species). The method involves contacting the process mixture with an anion exchange (AEX) adsorbent in an aqueous salt solution under loading conditions that permit both the target and non-target proteins to bind to the AEX adsorbent and allowing the excess target molecule to pass through the column and subsequently recovering the bound target protein with a wash at the same aqueous salt solution used in the equilibration (i.e. pre-loading) condition.

Source Material—

The antibody used in this study was derived from cell culture conditions employing both chemically defined media (CDM) and hydrolysate media. The antibody was captured from the clarified harvest through affinity chromatography (Protein-A, GE MabSuRe) where the eluate is in a buffer system of about 20 mM acetic acid at a pH of about 4.2.

Induced pH Gradient Anion Exchange Chromatography—

POROS 50 PI (Applied Biosystems) resin was packed in 1.0 cm×10.0 cm (OmniFit) column. The column was equilibrated in a two-component buffer containing acetate as the anion and either tromethalmine (Tris) or arginine as the cation. In these experiments, the anion (i.e. acetate) concentration was held constant and the cation (Tris/Arginine) was added to achieve the desired pH. Induced pH gradients were initially performed, without protein, by equilibrating the column with an Acetate/Tris or Acetate/Arginine buffer at pH 9.0 followed by a step change of the equivalent buffer at pH 7.0. Induced pH gradients without protein were run at controlled acetate concentrations of 5 mM, 10 mM, 20 mM, and 30 mM.

The POROS 50 PI column was then loaded with 20 g/L of D2E7 in 5 mM Acetate/Tris (or Arginine) pH 9.0, followed by a 10 column volume (CV) isocratic wash, and then an induced pH gradient elution with a step change in the running buffer to 5 mM Acetate/Tris (or Arginine) pH 7.0. The column was then regenerated (5 CVs of 100 mM acetate+1 M NaCl), cleaned in place (3 CVs 1M NaOH, 60 min hold), and stored (5 CVs 20% ethanol). During elution, the column effluent was fractionated into 0.5×CV and analyzed for UV280, WCX-10, and SEC (described below). The D2E7 AEX-load was prepared by diluting the source material described above with Milli-Q water to 5 mM acetate and titrating with arginine to the desired pH.

Flow-Through Anion Exchange Chromatography—

Using the induced pH gradient results, an operational pH was selected to operate the POROS 50 PI column in flow-through mode. The pH was selected (e.g. pH 8.8) to optimize the resolution between the acidic species and Lysine variants. The first run was performed by loading 150 g/L in a 5 mM Acetate/Arginine pH 8.8 buffer system, followed with a 20 CV isocratic wash. A FTW fraction was collected from 50-150 mAU and analyzed for UV280, WCX-10, and SEC. The results from this run are shown in Table 3. This run was able to reduce acidic species by 60% and remove almost all detectable high molecular weight species (i.e. aggregates) with about 68% recovery.

TABLE 3

Acidic species and aggregates reduction by AEX

| AEX Poros 50PI, 150 g/L FT, 5 mM Acetate/ Arginine pH 8.8 | Acidic Species | | SEC | | |
|---|---|---|---|---|---|
| | AR1 + 2 | LysSum | HMW | Mono | LMW |
| AEX Load (t = 0) | 17.805 | 81.685 | 1.704 | 97.947 | 0.348 |
| AEX Load (t = 10 days, 4° C.) | 19.711 | 79.746 | 1.975 | 97.831 | 0.194 |
| AEX FTW (t = 0) | 7.085 | 92.103 | 0.019 | 99.889 | 0.092 |
| AEX FTW (t = 10 days, 4° C.) | 8.069 | 91.773 | 0.04 | 99.853 | 0.107 |

The data presented here demonstrates a method for the fine purification of D2E7 from both product related (i.e. charge variants and molecular weight variants) impurities by loading the process stream to an anion exchange adsorbent under aqueous salt conditions (i.e. low conductivity and high pH) that permit both the target and non-target proteins to bind to the AEX adsorbent and allowing the excess target molecule to pass through the column and subsequently recovering the bound target protein with a wash at the same aqueous salt solution used in the equilibration (i.e. pre-loading) condition.

Example 3.2

Removal of Methylglyoxal-Modified Adalimumab Using CEX

This Example describes a process for purifying a target protein product from both process and product related impurities by using a cation exchange (CEX) technique. Specifically, a reversible binding method is disclosed for reducing product related charge variants (i.e. acidic species) of the target molecule. By way of example, the method may involve some or all of the following steps.

In one step, the process mixture is caused to be in contact with a cation exchange (CEX) adsorbent in an controlled aqueous buffer solution with pH and conductivity under loading conditions that permit both the target and non-target proteins to bind to the CEX adsorbent. The pH of the loading buffer is below the pI of the antibody molecule.

In another step, the charged variants, molecular variants and impurities are washed off using the same buffer conditions as the loading buffer. The product may then be eluted with a buffer having higher conductivity than that of the loading buffer.

In this Example, three antibody molecules were used. Adalimumab antibody was obtained from concentrated fractogel eluate in AY04 manufacturing process and CDM 300 L scale up run Protein A eluate. They were buffer exchanged into 29 mM Tris-acetate buffer pH 7.5 as CEX loading material.

Poros XS, (Applied Biosystems) strong CEX resin, CM Hyper D (Pall), weak CEX resin, Nuvia S (Bio-Rad) strong resin and GigaCap S 650 (Tosoh Biosciences) strong resin were packed in 1.0 cm×10.0 cm (OmniFit) columns. The column was equilibrated in a buffer system with appropriate pH and conductivity. The column load was prepared in the equilibration buffer and loaded on the column at 40 g protein/L resin followed by washing with the equilibration buffer for 20 CV. The antibody product was eluted out with 150 mM sodium chloride and 30 mM Tris-acetate buffer solution. 1M of NaCl was used for column regeneration and 1M of NaOH solution was used for column cleaning.

Four buffer/salt systems, sodium chloride/Tris-acetate, Tris-acetate, Ammonium sulfate/Tris-acetate and arginine/Tris-acetate at different pH and conductivity were evaluated. The buffer conditions are listed in Table 4.

TABLE 4

Buffer conditions

| Resin | Buffer | pH | Conductivity |
|---|---|---|---|
| Poros XS (strong) | Tris-acetate | 7.5, 6.5, 5.5 | 3 conductivity for each pH |
| | Sodium chloride | 7.5, 6.5, 5.5 | 3 conductivity for each pH |
| | Ammonium sulfate | 7.5 | 3 conductivity for each pH |
| CM Hyper D (weak) | Tris-acetate | 7.5 | 3 conductivity |
| | Sodium chloride | 7.5, 6.8, 6.0 | 3 conductivity for each pH |
| | Ammonium sulfate | 7.5 | 3 conductivity |
| Nuvia S (strong) | Tris-acetate | 7.5 | 3 conductivity |
| | Sodium chloride | | 3 conductivity |
| | Ammonium sulfate | | 3 conductivity |
| GigaCap S 650 | Tris-acetate | 7.5 | 3 conductivity |

Figure 11:
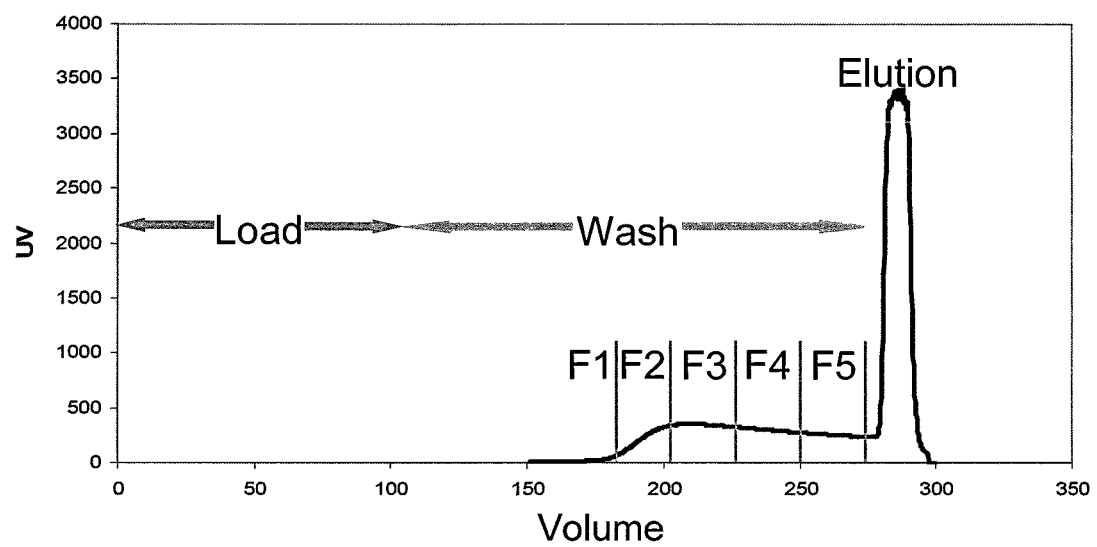
FIG. 11 shows the CEX chromatogram when reversible binding mode was performed using Adalimumab with a Tris-acetate buffer system.

A reversible binding mode was performed using Adalimumab with Tris-acetate buffer system. The loading utilized buffer at pH 7.5 and Tris concentration at 145 mM with 40 g protein/L resin. The column wash was fractionated. The wash fractions and elute pool were analyzed by UV280, WCX-10 and SEC assays. The chromatogram is shown in FIG. 11.

Example 4

Charge Variants Reduction in Adalimumab by Poros XS Resin

In this Example, different resins and buffer conditions were evaluated. The starting material contained 14% total AR and 3% AR1. Experiments were performed by varying resins and buffer conditions for acidic species removal. The results are described in the following sections.

Figure 12:
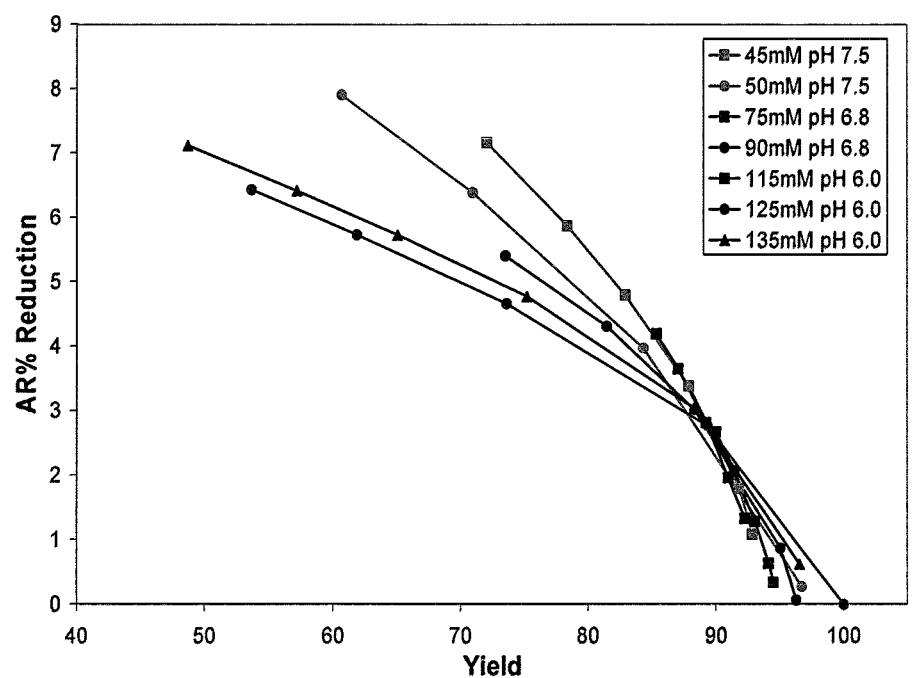
FIG. 12 shows the removal of acidic species by Poros XS resin with NaCl/Tris-acetate solution.

Experiments were performed on Poros XS resin using NaCl to vary the conductivity with a fixed 29 mM Tris-acetate buffer for pH control. Three pH levels were tested, pH 7.5, 6.8 and 6.0. Each pH was studied at conductivities wherein the amount of NaCl was varied. As shown in FIG. 12, acidic species can be removed by 3% with 90% yield. For further reduction in acidic species, the yields achieved vary under different buffer conditions. At pH 7.5 and 45 mM NaCl, the amount of acidic species was reduced by 6.8%, with 75% yield of Adalimumab. AR1 was significantly reduced to about zero percent, with a yield of 72% of Adalimumab, and to less than 0.5% with over 80% yield of Adalimumab, as shown in Table 5. The column wash was fractionated and specified as Fraction 1 to Fraction 5 by the order of adjacent to the eluate. The AR1, AR2, Lys sum versus yield was calculated based on the results of each fraction.

TABLE 5

AR1 removal versus yield by CEX

| Wash fractions | % AR1 | % AR2 | % Lys Sum | Yield (%) |
|---|---|---|---|---|
| Load | 2.9 | 12.1 | 84.3 | n/a |
| Eluate | 0 | 7.8 | 92.2 | 72 |
| Eluate + Fraction 1 | 0.3 | 8.8 | 91.0 | 79 |
| Eluate + Fraction 1 + Fraction 2 | 0.6 | 9.6 | 89.8 | 83 |
| Eluate + Fraction 1 + Fraction 2 + Fraction 3 | 1.6 | 10 | 88.4 | 88 |
| Eluate + Fraction 1 + Fraction 2 + Fraction 3 + _Fraction 4 | 2.2 | 10.9 | 86.8 | 92 |
| Eluate + Fraction 1 + Fraction 2 + Fraction 3 + _Fraction 4 + Fraction 5 | 2.9 | 11 | 86.1 | 93 |

In summary, methods for the purification of Adalimumab from product related impurities (i.e. charge variants and molecular weight variants) are disclosed. More particularly, the process stream may be loaded to a cation exchange adsorbent under appropriate aqueous conditions, wherein the pH and conductivity of the loading and wash buffer is below the pI of the target protein that permit both the target protein and impurities to bind to the CEX adsorbent. The acidic species and other impurities may then be washed off by using wash buffer which is the same as the loading buffer. Lastly, the bound target protein may be recovered by using a high conductivity aqueous solution.

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of this disclosure and the claims.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

1. Awdeh, Z. L., A. R. Williamson, and B. A. Askonas, *One cell-one immunoglobulin. Origin of limited heterogeneity of myeloma proteins*. Biochem J, 1970. 116(2): p. 241-8.
2. Liu, H., et al., *Heterogeneity of monoclonal antibodies*. Journal of Pharmaceutical Sciences, 2008. 97(7): p. 2426-2447.
3. Vlasak, J. and R. Ionescu, *Heterogeneity of Monoclonal Antibodies Revealed by Charge-Sensitive Methods*. Current Pharmaceutical Biotechnology, 2008. 9(6): p. 468-481.
4. Manning, M., et al., *Stability of Protein Pharmaceuticals: An Update*. Pharmaceutical Research, 2010. 27(4): p. 544-575.
5. Mizuochi, T., et al., Structural and numerical variations of the carbohydrate moiety of immunoglobulin G. J Immunol, 1982. 129(5): p. 2016-20.
6. Parekh, R. B., et al., Association of rheumatoid arthritis and primary osteoarthritis with changes in the glycosylation pattern of total serum IgG. Nature, 1985. 316(6027): p. 452-7.
7. Jefferis, R., *Glycosylation of Recombinant Antibody Therapeutics*. Biotechnology Progress, 2005. 21(1): p. 11-16.
8. Reed J, H., Processing of C-terminal lysine and arginine residues of proteins isolated from mammalian cell culture. Journal of Chromatography A, 1995. 705(1): p. 129-134.
9. Johnson, K. A., et al., Cation exchange HPLC and mass spectrometry reveal C-terminal amidation of an IgG1 heavy chain. Analytical Biochemistry, 2007. 360(1): p. 75-83.
10. Moorhouse, K. G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
11. Harris, R. J., et al., *Identification of multiple sources of charge heterogeneity in a recombinant antibody*. Journal of Chromatography B: Biomedical Sciences and Applications, 2001. 752(2): p. 233-245.
12. Huang, L., et al., *In Vivo Deamidation Characterization of Monoclonal Antibody by LC/MS/MS*. Analytical Chemistry, 2005. 77(5): p. 1432-1439.
13. Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub 2007 Dec. 8.

14. Zhang, W. and M. J. Czupryn, *Free Sulfhydryl in Recombinant Monoclonal Antibodies*. Biotechnology Progress, 2002. 18(3): p. 509-513.
15. Chumsae, C., G. Gaza-Bulseco, and H. Liu, Identification and localization of unpaired cysteine residues in monoclonal antibodies by fluorescence labeling and mass spectrometry. Anal Chem, 2009. 81(15): p. 6449-57.
16. Xiang, T., C. Chumsae, and H. Liu, Localization and Quantitation of Free Sulfhydryl in Recombinant Monoclonal Antibodies by Differential Labeling with 12C and 13C Iodoacetic Acid and LCâ''MS Analysis. Analytical Chemistry, 2009. 81(19): p. 8101-8108.
17. Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
18. Jakubowski, H., *Protein N-homocysteinylation: implications for atherosclerosis*. Biomedicine & Pharmacotherapy, 2001. 55(8): p. 443-447.
19. Chumsae, C., et al., Comparison of methionine oxidation in thermal stability and chemically stressed samples of a fully human monoclonal antibody. Journal of Chromatography B, 2007. 850(1-2): p. 285-294.
20. Zhang, B., et al., Unveiling a Glycation Hot Spot in a Recombinant Humanized Monoclonal Antibody. Analytical Chemistry, 2008. 80(7): p. 2379-2390.
21. Quan, C., et al., A study in glycation of a therapeutic recombinant humanized monoclonal antibody: Where it is, how it got there, and how it affects charge-based behavior. Analytical Biochemistry, 2008. 373(2): p. 179-191.
22. Cordoba, A. J., et al., *Non-enzymatic hinge region fragmentation of antibodies in solution*. Journal of Chromatography B, 2005. 818(2): p. 115-121.
23. Liu, H., G. Gaza-Bulseco, and E. Lundell, *Assessment of antibody fragmentation by reversed-phase liquid chromatography and mass spectrometry*. J Chromatogr B Analyt Technol Biomed Life Sci, 2008. 876(1): p. 13-23. Epub 2008 Oct. 15.
24. U.S. Pat. No. 6,090,382.

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

I claim:

1. A method for purifying a composition comprising adalimumab, the method comprising:
   (a) contacting a cation exchange adsorbent with a composition comprising adalimumab and adalimumab comprising one or more methylglyoxal (MGO)-modified arginine amino acids at position 30 (R30) of SEQ ID NO. 1, position 93 (R93) of SEQ ID NO. 1, position 108 (R108) of SEQ ID NO. 1, position 16 (R16) of SEQ ID NO. 2, position 259 (R259) of SEQ ID NO. 2, position 359 (R359) of SEQ ID NO. 2, or position 420 (R420) of SEQ ID NO. 2;
   (b) removing adalimumab comprising one or more methylglyoxal (MGO)-modified arginine amino acids from the cation exchange adsorbent; and
   (c) subsequently eluting the adalimumab from the cation exchange adsorbent using an elution buffer.

2. The method of claim 1 wherein the composition of step (a) comprises adalimumab comprising a methylglyoxal (MGO)-modified arginine amino acid at position 30 (R30) of SEQ ID NO. 1.

3. The method of claim 1 wherein the composition of step (a) comprises adalimumab comprising a methylglyoxal (MGO)-modified arginine amino acid at position 93 (R93) of SEQ ID NO. 1.

4. The method of claim 1 wherein the composition of step (a) comprises adalimumab comprising a methylglyoxal (MGO)-modified arginine amino acid at position 108 (R108) of SEQ ID NO. 1.

5. The method of claim 1 wherein the composition of step (a) comprises adalimumab comprising a methylglyoxal (MGO)-modified arginine amino acid at position 16 (R16) of SEQ ID NO. 2.

6. The method of claim 1 wherein the composition of step (a) comprises adalimumab comprising a methylglyoxal (MGO)-modified arginine amino acid at position 259 (R259) of SEQ ID NO. 2.

7. The method of claim 1 wherein the composition of step (a) comprises adalimumab comprising a methylglyoxal (MGO)-modified arginine amino acid at position 359 (R359) of SEQ ID NO. 2.

8. The method of claim 1 wherein the composition of step (a) comprises adalimumab comprising a methylglyoxal (MGO)-modified arginine amino acid at position 420 (R420) of SEQ ID NO. 2.

9. The method of claim 1 wherein the adalimumab and adalimumab comprising one or more methylglyoxal (MGO)-modified arginine amino acids are expressed in Chinese hamster ovary cells using chemically defined media.

10. The method of claim 1 wherein at least 90% of the adalimumab comprising one or more methylglyoxal (MGO)-modified arginine amino acids is removed in step (b).

11. The method of claim 1 wherein at least 99% of the adalimumab comprising one or more methylglyoxal (MGO)-modified arginine amino acids is removed in step (b).

12. The method of claim 1 wherein a loading buffer having a pH lower than the pI of the elution buffer of step (c) is used in contacting step (a).

13. The method of claim 12 wherein the loading buffer has a pH ranging from about 5.5 to about 7.5, and the loading buffer is selected from the group consisting of sodium chloride/Tris-acetate, Tris-acetate, Ammonium sulfate/Tris-acetate, arginine/Tris-acetate, and any combination thereof.

14. The method of claim 1 wherein the elution buffer is selected from the group consisting of sodium chloride/Tris-acetate, Tris-acetate, Ammonium sulfate/Tris-acetate, arginine/Tris-acetate, and any combination thereof, and wherein said elution buffer comprises a salt at a concentration ranging from about 20 mM to about 200 mM.

15. The method of claim 14 wherein the salt in the elution buffer is sodium chloride.

16. The method of claim 14 wherein the pH of the elution buffer is between 5.5 and 9.0.

17. The method of claim 1 wherein the adalimumab comprising one or more methylglyoxal (MGO)-modified arginine amino acids is removed in step (b) using a wash buffer.

18. The method of claim 17 wherein the wash buffer is the same chemical species as the loading buffer.

19. The method of claim 17 wherein the conductivity of the elution buffer is higher than the conductivity of the wash buffer.

20. A method for purifying a composition comprising adalimumab, the method comprising:
  (a) contacting a cation exchange adsorbent with a composition comprising adalimumab and adalimumab comprising one or more hydroxylimidines at position 30 (R30) of SEQ ID NO. 1, position 93 (R93) of SEQ ID NO. 1, position 108 (R108) of SEQ ID NO. 1, position 16 (R16) of SEQ ID NO. 2, position 259 (R259) of SEQ ID NO. 2, position 359 (R359) of SEQ ID NO. 2, or position 420 (R420) of SEQ ID NO. 2;
  (b) removing adalimumab comprising one or more hydroxylimidines from the cation exchange adsorbent; and
  (c) subsequently eluting the adalimumab from the cation exchange adsorbent using an elution buffer.

21. The method of claim 20 wherein the composition of step (a) comprises adalimumab comprising a hydroxylimidine at position 30 (R30) of SEQ ID NO. 1.

22. The method of claim 20 wherein the adalimumab and adalimumab comprising one or more hydroxylimidines are expressed in Chinese hamster ovary cells using chemically defined media.

23. The method of claim 20 wherein at least 90% of the adalimumab comprising one or more hydroxylimidines is removed in step (b).

24. The method of claim 20 wherein at least 99% of the adalimumab comprising one or more hydroxylimidines is removed in step (b).

25. A method for purifying a composition comprising adalimumab, the method comprising:
  (a) contacting a cation exchange adsorbent with a composition comprising adalimumab and adalimumab comprising one or more hydroimidazolones at position 30 (R30) of SEQ ID NO. 1, position 93 (R93) of SEQ ID NO. 1, position 108 (R108) of SEQ ID NO. 1, position 16 (R16) of SEQ ID NO. 2, position 259 (R259) of SEQ ID NO. 2, position 359 (R359) of SEQ ID NO. 2, or position 420 (R420) of SEQ ID NO. 2;
  (b) removing adalimumab comprising one or more hydroimidazolones from the cation exchange adsorbent; and
  (c) subsequently eluting the adalimumab from the cation exchange adsorbent using an elution buffer.

26. The method of claim 25 wherein the composition of step (a) comprises adalimumab comprising a hydroimidazolone at position 30 (R30) of SEQ ID NO. 1.

27. The method of claim 25 wherein the adalimumab and adalimumab comprising one or more hydroimidazolones are expressed in Chinese hamster ovary cells using chemically defined media.

28. The method of claim 25 wherein at least 90% of the adalimumab comprising one or more hydroimidazolones is removed in step (b).

29. The method of claim 25 wherein at least 99% of the adalimumab comprising one or more hydroxylimidines is removed in step (b).

* * * * *